United States Patent
Ning

(10) Patent No.: US 6,480,565 B1
(45) Date of Patent: Nov. 12, 2002

(54) APPARATUS AND METHOD FOR CONE BEAM VOLUME COMPUTED TOMOGRAPHY BREAST IMAGING

(75) Inventor: Ruola Ning, Penfield, NY (US)

(73) Assignee: University of Rochester, Rochester, NY (US)

( * ) Notice: Subject to any disclaimer, the term of this patent is extended or adjusted under 35 U.S.C. 154(b) by 23 days.

(21) Appl. No.: 09/640,713

(22) Filed: Aug. 18, 2000

Related U.S. Application Data

(60) Provisional application No. 60/166,223, filed on Nov. 18, 1999.

(51) Int. Cl.⁷ .................................................. A61B 6/04
(52) U.S. Cl. ........................................ 378/37; 378/20
(58) Field of Search ................................ 378/4, 15, 20, 378/37, 988

(56) References Cited

U.S. PATENT DOCUMENTS

| | | | |
|---|---|---|---|
| 3,973,126 A | * | 8/1976 | Redington et al. ............ 378/37 |
| 4,015,836 A | | 4/1977 | Redington et al. |
| 5,170,439 A | | 12/1992 | Zeng et al. |
| 5,257,183 A | | 10/1993 | Tam |
| 5,278,884 A | | 1/1994 | Eberhard et al. |
| 5,365,560 A | | 11/1994 | Tam |
| 5,390,226 A | | 2/1995 | Tam |
| 5,400,255 A | | 3/1995 | Hu |
| 5,459,769 A | | 10/1995 | Brown |
| 5,461,650 A | | 10/1995 | Tam |
| 5,517,602 A | | 5/1996 | Natarajan |
| 5,671,265 A | | 9/1997 | Andress |
| 5,802,133 A | | 9/1998 | Kawai et al. |
| 5,949,811 A | | 9/1999 | Baba et al. |
| 5,999,587 A | | 12/1999 | Ning et al. |
| 6,075,836 A | | 6/2000 | Ning |
| 6,292,531 B1 | * | 9/2001 | Hsieh ........................... 378/37 |
| 2001/0038681 A1 | * | 11/2001 | Stanton et al. ................. 378/55 |

FOREIGN PATENT DOCUMENTS

| | | |
|---|---|---|
| EP | 0 948 930 | 10/1999 |
| WO | WO 99 01066 | 1/1999 |

OTHER PUBLICATIONS

P. Grangeat, "Mathematical Framework of Cone Beam 3D Reconstruction via the First Derivative of the Radon Transform", *Mathematical Methods in Tomography*, Herman, Lewis, Natterer (eds.), Lecture Notes in Mathematics, No. 1497, pp. 66–97, Spring Verlag (1990).

L.A. Feldkamp et al., "Practical cone–beam algorithm", J. Opt. Soc. Am. A/vol. 1, No. 6, Jun. 1984 pp. 612–619.

Y. Weng et al., A Reconstruction Algorithm for Helical Cone–Beam SPECT, IEEE Transactions on Nuclear Science, vol. 40, No. 4, Aug. 1993, pp. 1092–1101.

(List continued on next page.)

*Primary Examiner*—David P. Porta
(74) *Attorney, Agent, or Firm*—Blank Rome Comisky & McCauley LLP

(57) ABSTRACT

Cone beam volume CT mammography is performed with a gantry frame on which a cone-beam radiation source and a digital area detector are mounted. The patient rests on an ergonomically designed table with a hole or two holes to allow one breast or two breasts to extend therethrough such that the gantry frame surrounds that breast. The gantry frame is rotatable so that the radiation source and the detector move in a circular orbit around the breast. In addition, the gantry frame is movable to describe a geometry other than a simple circle orbit, such as a circle plus one or more lines or a spiral.

63 Claims, 13 Drawing Sheets

OTHER PUBLICATIONS

Bruce D. Smith, "Image Reconstruction from cone–Beam Projections: Necessary and Sufficient Conditions and Reconstruction Methods" IEEE Transactions on Medical Imaging, vol. M–4, No. 1, Mar. 1985, pp. 14–25.

B. Smith, "Cone–beam tomography: recent advances and a tutorial review", Optical Engineering, vol. 29, No. 5, May 1990, pp. 524–534.

H. Tuy, "An inversion formula for cone–beam reconstruction", SIAM J. Appl. Math, vol. 43, No. 3, Jun. 1983, pp. 546–552.

Jaffray D.C. et al., *Performance of a Volumetric CT Scanner Based Upon a Flat–Panel Imager*, Proceedings of the 1999 Medical Imaging–Physics of Medical Imaging Conference, San Diego, CA, USA vol. 3659, No. 1, pp 21–23, Feb. 1999.

Ivanovic M. et al., *Multi–Pinhole Collimator Optimization for High Resolution SPECT Imaging*, 1997 IEEE Nuclear Science Symposium Conference Record, Albuquerque, NM, USA, pp. 9–15, Nov. 1997.

\* cited by examiner

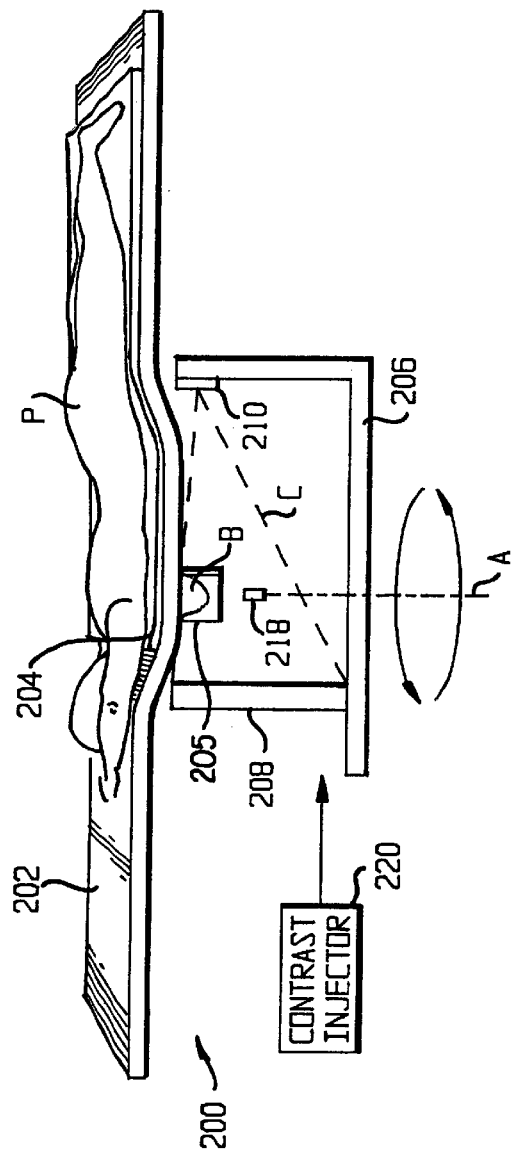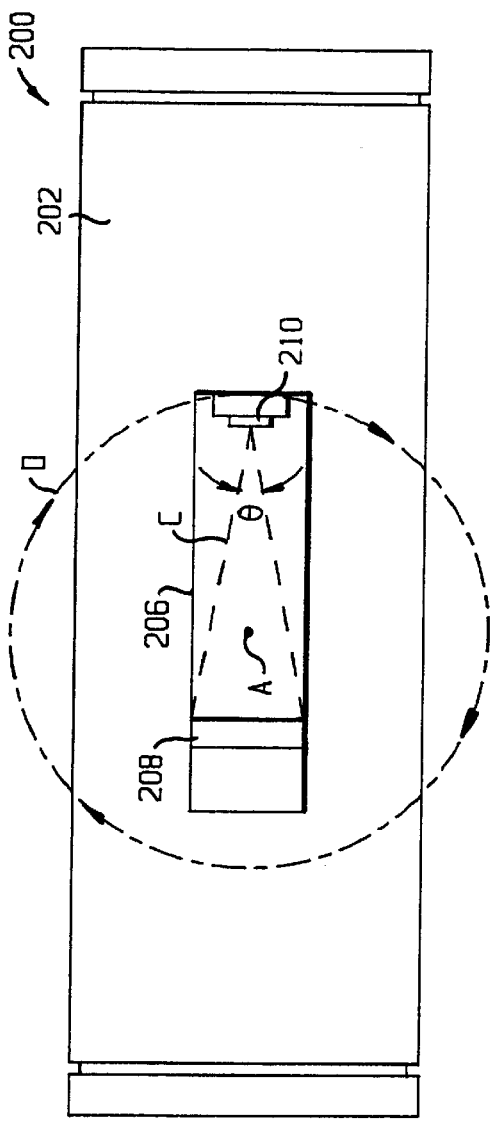

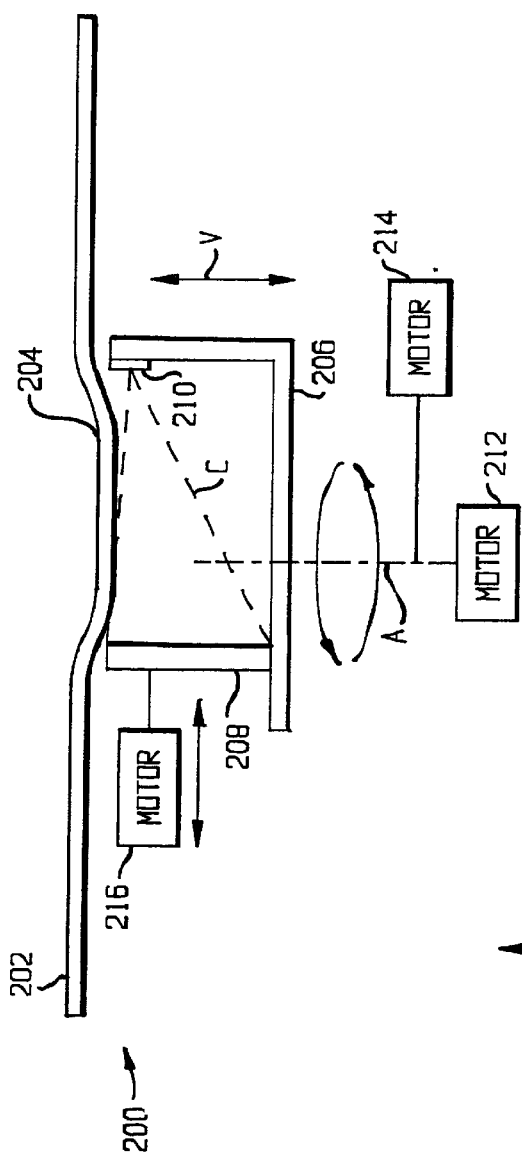
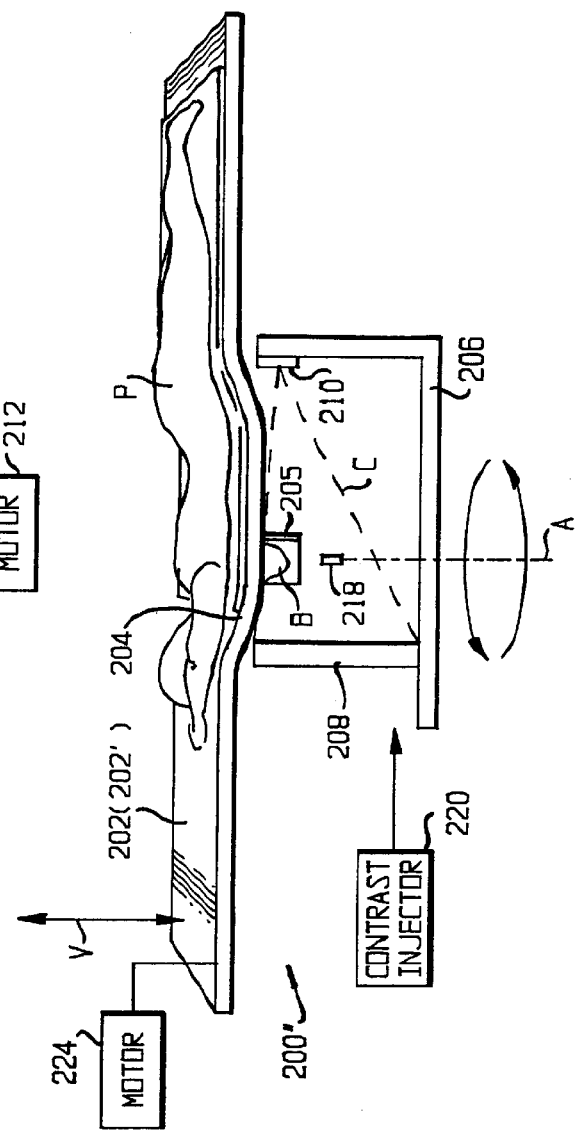

APPARATUS AND METHOD FOR CONE BEAM VOLUME COMPUTED TOMOGRAPHY BREAST IMAGING

REFERENCE TO RELATED APPLICATION

This application claims the benefit of U.S. Provisional Application No. 60/166,223, filed Nov. 18, 1999, whose disclosure is hereby incorporated by reference in its entirety into the present disclosure.

BACKGROUND OF THE INVENTION

Breast cancer represents a significant health problem. More than 180,000 new cases are diagnosed, and nearly 45,000 women die of the disease each year in the United States.

The clinical goal of breast imaging is to detect tumor masses when they are as small as possible, preferably less than 10 mm in diameter. It is reported that women with mammographically detected, 1–10 mm invasive breast carcinoma have a 93% 16-year survival rate.

Conventional screen film mammography is the most effective tool for the early detection of breast cancer currently available. However, mammography has relatively low sensitivity to detect small breast cancers (under several millimeters). Specificity and the positive predictive value of mammography remain limited owing to an overlap in the appearances of benign and malignant lesions. Limited sensitivity and specificity in breast cancer detection of mammography are due to its poor contrast detectability, which is common for all types of projection imaging techniques (projection imaging can only have up to 10% contrast detectability). The sensitivity with which conventional mammography can identify malignant tumors in the preclinical phase will largely be affected by the nature of the surrounding breast parenchyma. Detection of calcifications will be influenced to a lesser degree by the surrounding tissue. The perception of breast masses without associated calcification, representing the majority of tumors in patients with detected carcinomas, is greatly influenced by the mammographic parenchymal pattern. Thus conventional mammography is often not able to directly detect tumors of a few millimeters due to poor low contrast resolution. Conventional mammography requires ultrahigh resolution (50–100 $\mu$m/pixel) to image microcalcifications to compensate for its poor contrast resolution. Mammography fails to initially demonstrate 30%–35% of cancers. In addition, not all breast cancers detected with mammography will be found early enough to cure. At best, it appears that conventional mammography can reduce the death rate by up to 50%. This is an important gain, but there is considerable room for improvement in early detection of breast cancer.

Relatively low specificity of mammography results in biopsy for indeterminate cases despite the disadvantages of higher cost and the stress it imposes on patients. There is a need for more accurate characterization of breast lesions in order to reduce the biopsy rate and false-positive rate of biopsy.

There are several radiological or biological characteristics of breast carcinoma that can be imaged. First, carcinoma has different x-ray linear attenuation coefficients from surrounding tissues, as shown in FIG. 1. Second, carcinoma has a substantially higher volume growth rate compared to a benign tumor, which lacks growth. Third, carcinoma has patterns distinguishable from those of a benign tumor. Fourth, benign tumors show no contrast enhancement after intravenous contrast injection. Fifth, the presence of neovascularity can indicate cancer. Conventional mammography relies mainly on the first characteristic and partially uses the third characteristic for breast cancer detection. Since mammography is a two-dimensional static imaging technique, it cannot provide any information regarding characteristics 2, 4, or 5.

Currently, radiological evaluation of breast cancer is important not only for early detection of disease, but also for staging and monitoring response to treatment. So far, conventional screen film mammography has been shown to be the most cost-effective tool for the early detection of breast cancer. The specificity and positive predictive value of mammography, however, remain limited, owing to an overlap in the appearances of benign and malignant lesions and to poor contrast detectability, which is common for all projection imaging techniques. Projection imaging can have only up to 10% contrast detectability. Biopsy is therefore often necessary in indeterminate cases, despite the disadvantages of higher cost and the stress it imposes on patients. There is therefore a need for more accurate characterization of breast lesions in order to reduce the biopsy rate.

In the last decade, MRI of the breast has gained a role in clarifying indeterminate cases after mammography and/or ultrasound, especially after breast surgery and in detecting multifocal breast cancers. However, the integration of MR into routine clinical practice has been hampered by a number of limitations, including long scanning times and the high cost of MR examinations. Additionally, many patients cannot undergo MR because of MR contraindications (e.g., aneurysm clips, pacemaker) or serious claustrophobia.

Characterization of breast lesions on MR has been based largely on the differential rates of enhancement between benign and malignant lesions. The constant trade-off between spatial and temporal resolution in MR has made it difficult to achieve the spatial resolution necessary for improved lesion characterization.

Standard fan beam computed tomography (CT), including spiral CT, has been evaluated as a potential tool for the characterization of breast lesions. Most previous work has been based on the traditional or helical technique using the whole body scanner. That technique, however, suffers from a number of disadvantages including significantly increased radiation exposure due to the fact that standard CT can not be used to target only the breast, so that the majority of x-rays are wasted on whole body scanning. That leads to relatively low in-plane spatial resolution (typically 1.0 lp/mm), even lower through plane resolution (less than or equal to 0.5 lp/mm in the direction perpendicular to slices), and prolonged volume scanning times, since spiral CT scans the whole volume slice by slice and takes 120 seconds for the whole breast scan. It still takes 15–30 seconds for the latest multi-ring spiral CT for 1 mm/slice and 12 cm coverage.

Ultrasound has poor resolution in characterizing lesion margins and identifying microcalcifications. Ultrasound is also extremely operator dependent.

In addition, for conventional mammography, compression is essential for better low-contrast detectability. However, patients are uncomfortable even though compression may not be harmful to them.

SUMMARY OF THE INVENTION

It will be readily apparent from the foregoing that a need exists in the art for a mammography imaging system and method which overcome the above-noted limitations of conventional techniques.

It is therefore a primary object of the invention to provide a clinically useful three-dimensional mammography technique for accurate detection of breast cancer.

It is another object of the invention to provide a mammography technique which can operate with only a single fast volume scanning to provide true three-dimensional (3D) description of breast anatomy with high isotropic spatial resolution and lesion location, while conventional mammography only provides two-dimensional projection images.

It is yet another object of the invention to provide imaging technique to tomographically isolate a breast tumor from the other objects in adjacent planes, consequently eliminate overlap and remove superimposed structures.

It is yet another object of the invention to provide higher contrast resolution compared with conventional mammography and adequate spatial resolution for breast cancer detection.

It is yet another object of the invention to improve the detectability of breast carcinoma (tumors) of a few millimeters in size due to much better low contrast resolution, compared to conventional mammography.

It is yet another object of the invention to provide high resolution volume of interest (VOI) reconstruction mode for target imaging and better characterization of breast tumors three-dimensionally compared with conventional mammography.

It is yet another object of the invention to provide a three-dimensional tomographic reconstruction technique to detect the difference of x-ray linear attenuation coefficients of carcinoma from surrounding tissue. (carcinoma has different x-ray linear attenuation coefficients from surrounding tissue.)

It is yet another object of the invention to provide accurate depiction of breast tumor border pattern for better characterization of breast tumors compared with conventional mammography (carcinoma has distinguishable border patterns from those of a benign tumor).

It is yet another object of the invention to improve specificity in breast cancer detection compared with conventional mammography by allowing more precise measurement of change in lesion volume over relatively short periods of time (carcinoma has a much faster volume growth rate than a benign tumor).

It is yet another object of the invention to provide a mammography technique usable with intravenous (IV) injection of iodine contrast to improve detection and characterization of breast tumors by allowing an assessment of lesion vascularity and enhancement rate (a benign tumor and a malignant tumor have different contrast enhancement rates).

It is yet another object of the invention to provide a mammography technique usable with intravenous (IV) injection of iodine contrast to assess breast tumor angiogenesis non-invasively.

It is yet another object of the invention to increase patient comfort by decreasing the amount of breast compression required.

It is yet another object of the invention to use CBVCTM image-based volume growth measurement technique (both positive growth and negative growth) to determine malignancy of breast tumors and to monitor the effect of breast cancer treatment (this method can be also used for other malignancies, such as lung cancer).

It is yet another object of the invention to use higher x-ray energies than those used in conventional mammography, for breast imaging to increase penetration, improve image quality and reduce patient radiation dose.

It is yet another object of the invention to perform multi-resolution volume tomographic reconstruction from the same set of projection images to improve the dectectibility of microcacification and breast carcinoma (tumors), better characterize breast tumors, and consequently reduce the total accumulative dose for patient.

It is yet another object of the invention to use a CBVCTM image-based computer aided diagnostic technique to improve the detectibility and characterization of breast carcinoma (tumors).

It is yet another object of the invention to improve sensitivity of breast cancer detection and thereby further reduce mortality of breast cancer by detecting small breast cancers that can not be detected by conventional mammography.

It is yet another object of the invention to improve specificity of mammography and greatly reduce the biopsy rate.

It is yet another object of the invention to provide adequate image quality for the mammographically dense breast.

It is yet another object of the invention to facilitate 3D image-guided biopsy procedures.

It is yet another object of the invention to allow accurate assessment of cancer extent for both better pre-surgical planning, especially in limited resections, and radiation therapy treatment planning, as well as for more accurate monitoring of breast cancer response to treatments.

To achieve the above and other objects, the present invention is directed to a system and method incorporating a cone beam volume tomographic reconstruction technique with the recently developed flat panel detector to achieve cone beam volume computed tomographic mammography (CBVCTM). With a cone beam geometry and a flat panel detector, a flat panel-based cone beam volume computed tomography mammography (CBVCTM) imaging system can be constructed, and three-dimensional (3D) reconstructions of a breast from a single fast volume scan can be obtained. In contrast to conventional mammography, the flat panel-based CBVCTM system can provide the ability to tomographically isolate an object of interest (e.g., a lesion) from an object (e.g., other lesion or calcification) in adjacent planes. The 3D tomographic reconstructions eliminate lesion overlap and provide a complete, true 3D description of the breast anatomy. In contrast to existing computed tomography (CT) with an intraslice resolution of 1.0 lp/mm and through plane resolution of 0.5 lp/mm, the CBVCTM reconstructions can have 2.0 lp/mm or better of isotropic spatial resolution (or, more generally, better than 1 lp/mm) along all three axes. The invention is further directed to an ultrahigh resolution volume of interest (VOI) reconstruction using the zoom mode of the flat panel detector to achieve up to 5.0 lp/mm resolution. Thus, CBVCTM can have many times better contrast detectability (tomographic imaging can have up to 0.1% contrast detectability) than that of conventional mammography.

Various scanning geometries can be used. It is contemplated that either a circle scan or a circle-plus-line (CPL) scan will be used, depending on the size of the breast. However, other geometries, such as spiral, can be used instead.

The present invention provides better detection of breast cancers, better lesion characterization, and more accurate preoperative and postoperative information on breast anatomy, thus reducing the negative biopsy rate.

The present imaging technique has significant clinical impact on breast cancer detection, diagnosis and the evaluation of the effectiveness of therapy. Because of its excellent low contrast detectability and high and isotropic resolution, the present invention significantly improves the accuracy of breast lesion detection, and hence greatly reduces the biopsy rate. The potential clinical applications of such a modality are in the imaging of the mammographically indeterminate lesions, the mammographically dense breast and the postsurgical breast. Currently, most mammographically indeterminate lesions end up being biopsied in order to arrive at a definitive diagnosis. It is well known that the usefulness of mammography in patients with dense breasts is limited and that additional imaging or biopsy is frequently required. The use of an imaging modality that has a capability for multi-planar and volumetric data acquisition has the potential to improve lesion characterization in dense breast tissue. The higher spatial resolution afforded CBVCTM can potentially improve the differentiation of recurrence and form of post-surgical changes.

The present invention provides very high-resolution tomographic images by zooming in on small lesions or specific regions within a tumor. Detailed interrogation of specific areas within a lesion, e.g., microcalcifications, necrotic and cystic as well as areas of intraductal extension enables more accurate characterization of breast lesions. The use of contrast material and dynamic imaging provides additional temporal information, which, together with morphological features, enhances specificity and reduces the biopsy rate.

Tumor angiogenesis is an independent prognostic indicator in breast cancer. Currently, angiogenesis is determined by assessing microvessel density in pathologic specimens. However, researchers have also detected good correlation between contrast enhancement and microvessel density. The use of contrast medium in an imaging modality that provides very high spatial and temporal resolution offers a non-invasive method to assess tumor angiogenesis. Additionally, the acquisition of volumetric data with 3D rendering allows multiplanar imaging and better presurgical planning, especially in limited resections.

In summary, the introduction of CBVCTM, with the potential for obtaining a very high spatial resolution tomographic images, offers improved lesion characterization in mammographically indeterminate breast lesions with a view to reducing the biopsy rate. It also offers the advantages of enhancing preoperative and postoperative planning.

CBVCTM has the capacity to provide information regarding characteristics 1–5 discussed above with reference to the prior art to improve lesion detection and characterization.

In a preferred embodiment, the patient lies face down on an ergonomic patient table having one or two breast holes. The gantry holding the x-ray source and the flat panel detector rotates below the table to image the breast or two breasts. To obtain projections other than simple circle projections, the gantry frame can be moved vertically, or the table can be moved vertically. One advantage of having two breast holes is to preserve the geometric relationship between the breasts. In an alternative embodiment, the patient stands before the gantry with straps to hold the patient still.

A further modification of the present invention uses an ultra-high-resolution volume-of-interest (VOI) reconstruction mode to focus on a suspicious lesion. The ultra-high-resolution VOI reconstruction mode is analogous to magnified mammography.

CBVCTM will provide very high-resolution tomographic images by zooming in on small lesions or specific regions within a tumor. Detailed interrogation of specific areas within a lesion (i.e. microcalcifications, necrosis and cysts as well as areas of intraductal extension without overlap structures) will enable more accurate characterization of breast lesions.

CBVCTM will potentially provide a non-invasive method to assess tumor angiogenesis. Recent work has established that tumor angiogenesis is an independent prognostic indicator in breast cancer. Currently, angiogenesis is determined by assessing microvessel density in pathologic specimens. However, researchers have also detected good correlation between contrast enhancement and microvessel density. The use of contrast media in an imaging modality that provides very high spatial and temporal resolution may offer a non-invasive method to assess tumor angiogenesis.

With the present invention, a CBVCTM scan can be completed rapidly, and several sets of scans can be performed continuously for dynamic contrast studies and angiogenesis studies.

Throughout the specification and claims, it will be understood that the present invention is not limited to mammography, but should instead be understood as broadly applicable to breast imaging in general.

BRIEF DESCRIPTION OF THE DRAWINGS

A preferred embodiment of the present invention will be set forth in detail with reference to the drawings, in which:

FIGS. 2A–2C show a schematic diagram of a cone beam volume CT mammography scanner according to the preferred embodiment;

FIG. 2F shows yet another variation of the scanner of FIGS. 2A–2C;

DETAILED DESCRIPTION OF THE PREFERRED EMBODIMENT

Figure 1:
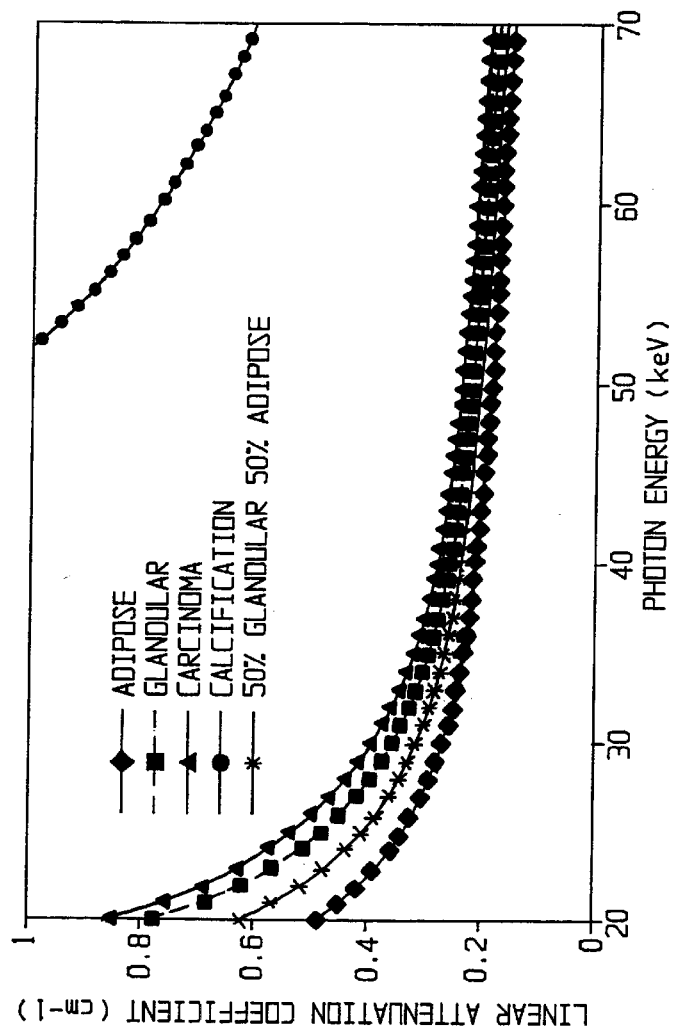
FIG. 1 shows the linear attenuation coefficients of various tissues which may be found in a healthy or diseased breast.

A preferred embodiment and an alternative embodiment of the present invention will now be set forth in detail with reference to the drawings, in which the same reference numerals refer to the same components throughout.

The limitations accompanying conventional mammography are addressed by incorporating a cone beam volume CT reconstruction technique with a flat panel detector. With cone beam geometry and a flat panel detector, a flat panel-based cone beam volume computed tomography mammography (CBVCTM) imaging system can be constructed as shown in FIGS. 2A–2F, and three-dimensional (3D) reconstructions of a breast from a single fast volume scan can be obtained. In contrast to conventional mammography, the flat panel-based CBVCTM system provides the ability to tomographically isolate an object of interest (e.g. a lesion) from the other objects in adjacent planes (e.g. other lesion or calcification). The 3D tomographic reconstructions eliminate lesion overlap and provide a complete, true 3D description of breast anatomy. In contrast to conventional computed tomography (CT) with an intraslice resolution of ~1.0 lp/mm and through plane resolution of 0.5 lp/mm, the CBVCTM reconstructions can have 2.0 lp/mm or better of isotropic spatial resolution. An ultrahigh resolution volume of interest (VOI) reconstruction can be produced by using the zoom mode of the flat panel detector to achieve up to 5.0 lp/mm or better resolution, depending on the size of x-ray focal spot and inherent detector resolution. An FPD-based CBVCTM can be built with slip ring technology. A slip ring is an electromechanical device allowing the transmission of electrical power, signals or both across a rotating interface. One source of slip rings is Fabricast, Inc., of South El Monte, Calif., U.S.A.

The schematic design of the CBVCTM scanner is shown in FIGS. 2A–2F. The CBVCTM scanner has an ergonomic patent table design and scanning geometry especially suitable for target imaging.

In the scanner 200, the patient P rests on an ergonomically formed table 202 so that the breast B to be scanned descends through a hole 204 in the table 202 into a breast holder 205. The breast holder 205, which will be described in greater detail below, forms the breast B into a cylindrical shape for scanning, which is more comfortable for most patients than the conventional flattened shape.

Below the table 202, a gantry 206 supports a detector 208 and an x-ray tube 210, one on either side of the breast holder 205. The gantry is turned by a motor 212 to be rotatable around an axis A passing through the breast holder 205, so that as the x-ray tube travels along an orbit O, the breast B remains in the path of a cone beam C emitted by the x-ray tube 210. The gantry is also movable by a motor 214 to go up and down along a vertical path V. Alternatively, the table 202 can be moved up and down along a vertical path V. The detector 208 can be moved toward and away from the axis A by a motor 216 to change the magnification factor if necessary.

To assure the geometric reproducibility of breast imaging and proper imaging of the chest wall, the breast holder 205 is relatively rigid and is made of a material with low x-ray attenuation. The breast holder is shown as being part of the table 202, but it can alternatively be made part of the gantry 206. The breast holder 205 pulls the breast out of the chest wall to assure proper imaging of the chest wall and applies a light and reproducible compression to form the breast into a cylindrical shape. There may be a cushion inside the breast holder to assure the patient's comfort. Then a piston 218 may be used to push the nipple toward the chest wall to reduce z-direction coverage by a couple of centimeters. That piston-pushing reduces the required cone angle of the x-ray beam. Consequently, with the piston-pushing, the majority of breast scans (for breasts <10 cm in height) may be achieved by using only the circular scan mode, and for a large breast, the number of required line projections may be reduced. In addition, the piston-pushing improves uniformity of breast thickness.

A contrast injector 220 can be provided for contrast enhanced tomographic imaging, angiogenesis studies and some other dynamic contrast studies. Various contrast injection media, such as iodine, are known in the art. It is not always necessary to inject a contrast medium into the patient.

Figure 2D:
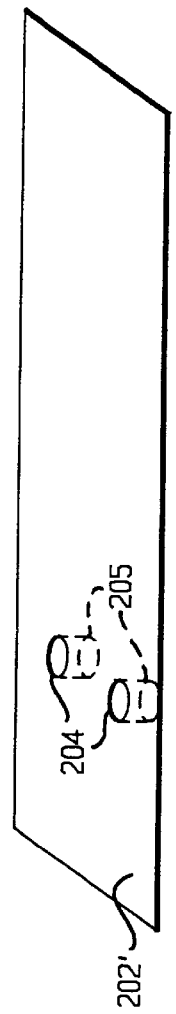
FIG. 2D shows one variation of the scanner of FIGS. 2A–2C.

The table 202 can be replaced with the table 202' of FIG. 2D. The table 202' is formed like the table 202, except that two breast holes 204 are provided, each with a breast holder 205. The table 202' is movable. One breast is moved into the imaging field and is scanned first. Then the other breast is moved into the imaging field and scanned. Thus, the geometric relationship between the breasts is preserved. Alternatively, two breasts with two breast holders can be scanned together.

Figure 2E:
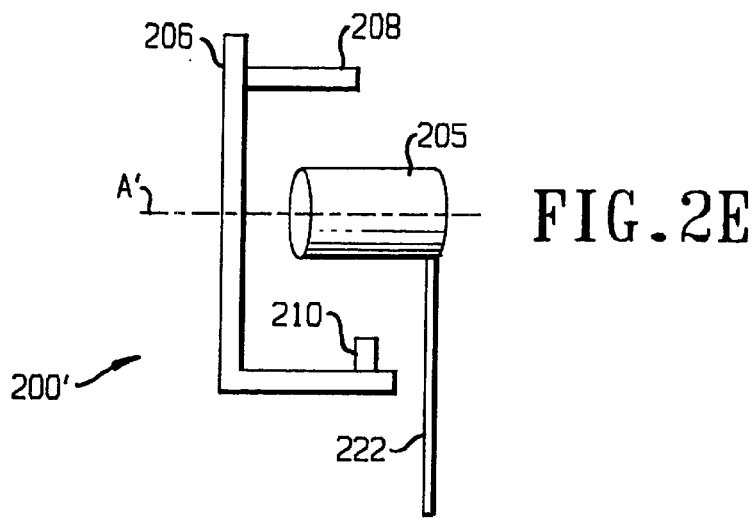
FIG. 2E shows another variation of the scanner of FIGS. 2A–2C.

Alternatively, the scan or scans can be performed while the patient is standing. As shown in FIG. 2E, in such a scanning system 200', a breast holder 205 is supported by a stand 222 to support a breast of a standing patient. Alternatively, two breast holders 205 can be provided on the stand 222. One breast is moved into the imaging field and is scanned first. Then the other breast is moved into the imaging field and scanned. Alternatively, two breasts with two breast holders can be scanned together. The gantry 206, holding the detector 208 and the x-ray tube 210, is oriented to rotate around a horizontal axis A' rather than the vertical axis A of FIGS. 2A–2C. In other respects, the system 200' can be like the system shown in FIGS. 2A–2C.

Still another variation is shown in FIG. 2F. The scanner 200" of FIG. 2F is based on either of the scanners 200 and 200' of FIGS. 2A–2E, except that the motor 214 is replaced by a motor 224 to move the table 202 or 202' up and down along the vertical path V. In that way, the gantry 206 does not have to move vertically.

Figure 3:
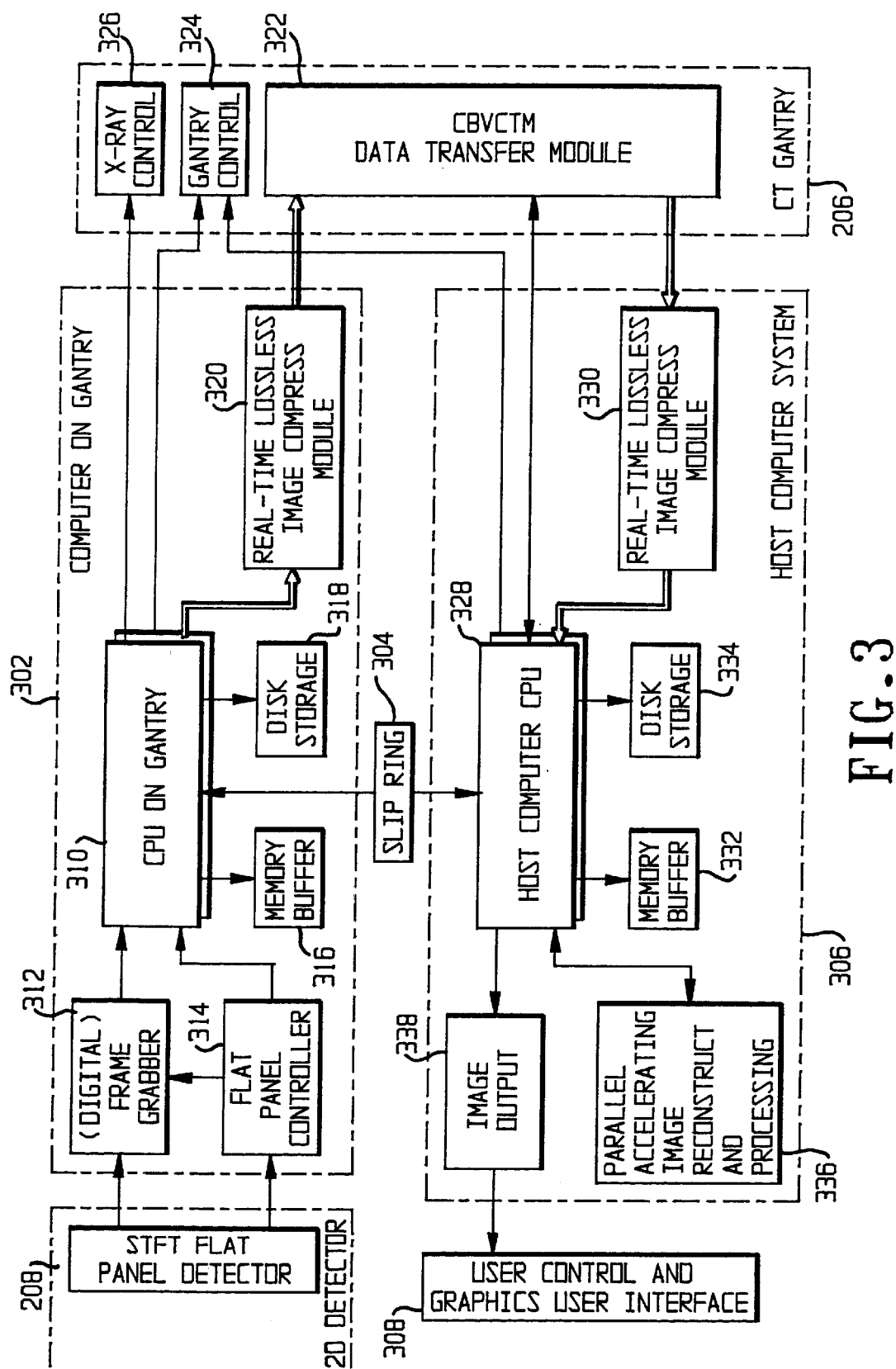
FIG. 3 shows a block diagram of the circuitry used in the scanner of FIGS. 2A–2F.

The circuitry of the scanner 200 is shown in FIG. 3. A computer 302 on the gantry 206 is connected through a slip ring 304 on a shaft of the gantry 206 to a host computer system 306. The computer 302 on the gantry 206 is also in communication with the detector 208, while both computers 302 and 306 are in communication with various other devices on the gantry 206, as explained below. The computer 306 is further in communication with a user control and graphics user interface 308.

In the computer 302 on the gantry 206, the CPU 310 is in communication with the detector 208 through a digital frame grabber 312 and a flat panel controller 314. The CPU 310 is also in communication with a memory buffer 316, disk storage 318 and a real-time lossless image compression module 320; through the compression module 320, the CPU 310 communicates with a CBVCTM data transfer module 322 on the gantry 206. The CPU 310 directly communicates with two other devices on the gantry, namely, the gantry control 324 and the x-ray control 326. The x-ray control 326 can control the exposure pulse length, exposure timing, and exposure pulse numbers. In addition, the x-ray control 326 can real-timely (dynamically) change x-ray exposure level from projection to projection to achieve optimal x-ray dose efficiency without degrading reconstructed image quality.

In the host computer system 306, a host computer CPU 328 communicates with the data transfer module 322, both directly and through a real-time image decompression module 330. The CPU 328 is also in communication with a memory buffer 332, disk storage 334 and a parallel accelerating image reconstruction and processing module 336. Through an image output 338, the CPU 328 communicates with the interface 308. The CPU's 310 and 328 communicate with each other through the slip ring 304. Also, although it is not shown in FIG. 3 for simplicity, all communication between components on the gantry 206 and the host computer system 306 take place through the slip ring 304.

The CPU 328 with the Parallel Accelerating Image Reconstruction and Processing Module 336 can perform multi-resolution volume tomographic reconstruction from the same set of projection images to improve the detectability of microcalcification and breast carcinoma (tumors), better characterize breast tumors and consequently reduce the total accumulative dose for the patient. The CPU 328 can also be used in a CBVCTM image-based computer aided diagnosis technique to improve the detectability and characterization of breast carcinoma.

The slip ring 304 and a fast gantry 206 permit optimal CPL scanning with a quasi-spiral scanning scheme and fast dynamic contrast studies. With that design, a CBVCTM scan can be completed within a few seconds, and several sets of scans can be performed continuously for dynamic contrast studies and angiogenesis studies. If the locus of an x-ray source and a detector is a single circle during cone beam scanning (single circle cone-beam geometry), an incomplete set of projection data is acquired. The incompleteness of the projection data results in some unavoidable blurring in the planes away from the central z-plane and resolution loss in the z direction. Using Feldkamp's algorithm which is based on a single circle cone beam geometry, the magnitude of the reconstruction error due to the incompleteness of projection data is increased with cone angle. Computer simulation indicates that for mammography imaging and an average breast size (10 cm in height or smaller), the reconstruction error is relatively small (<5%), and no streak artifacts can be observed. A modified Feldkamp's algorithm is used for small and average breast sizes (<10 cm in height), and a circle-plus-lines (CPL) cone beam orbit and its corresponding filter backprojection algorithm are used for a large breast (>10 cm in height). That approach practically solves the problem of the incompleteness of projection data from a single circle cone beam geometry for mammography scanning. A suitable modified Feldkamp's algorithm is taught in Hu, H., "A new cone beam reconstruction algorithm and its application to circular orbits," *SPIE* 1994; 2163:223–234. A suitable algorithm for circle-plus-a line is taught in Hu, H., "Exact regional reconstruction of longitudinally-unbounded objects using the circle-and-line cone beam tomographic," *Proc. SPIE*, Vol. 3032, pp. 441–444, 1997; and in Hu, H., "An improved cone-beam reconstruction algorithm for the circular orbit," *Scanning* 1996, 18:572–581. Modifications of those known algorithms which can be used in the present invention are taught in the following references: Wang X, Ning R: "Accurate and efficient image intensifier distortion correction algorithm for volume tomographic angiography," *Opt. Eng* 37(3) 977–983, 1998; and Wang X. and Ning R., "A cone beam reconstruction algorithm for a circle-plus-an arc acquisition geometry," *IEEE Trans Med Imag*, 1999:vol. 18(9), 815–824. The algorithms in the articles just cited are given as illustrative rather than limiting. Any other suitable algorithms can be used instead.

Figure 4:
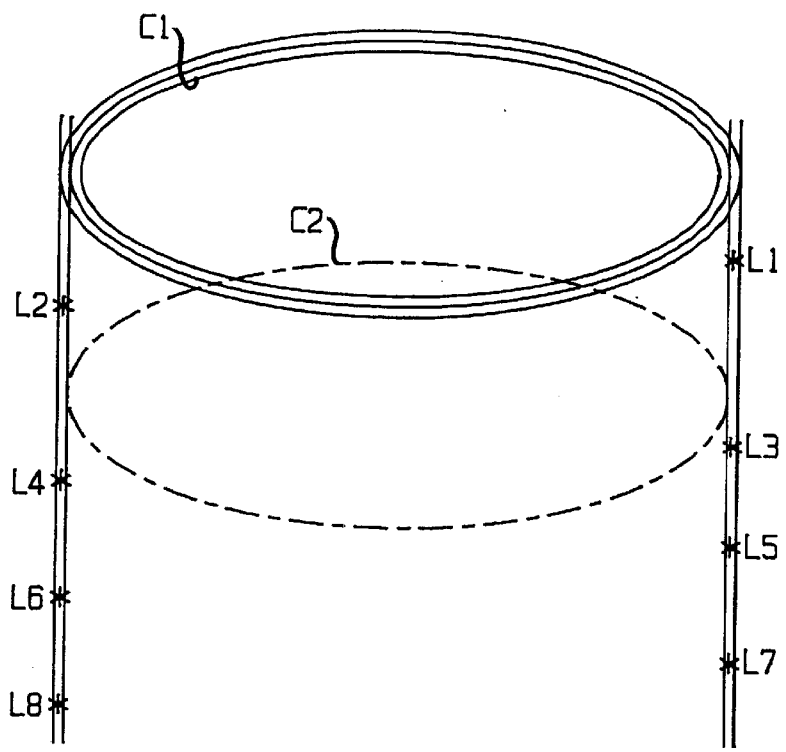
FIG. 4 shows a scanning geometry which can be implemented in the scanner of FIGS. 2A–2F.

The circular scan can be implemented with the CBVCTM scanner in the following manner: 1) position the patient's breast B into the hole 204 in the patient table 202 with a lightly-compressed breast holder 205 to form the breast into a cylinder-like shape; 2) rotate the gantry 206 to acquire a set of circle projections over 180° plus cone angle, or over N×360°, where N is a positive integer (1, 2, 3 ... ). The CPL scan can be implemented using a quasi-spiral scan with slip ring technology in the following three steps: 1) position the patient's breast B into the hole 204 in the patient table 202 with a lightly-compressed breast holder 205 to form the breast into a cylinder-like shape; 2) rotate the gantry 206 to acquire a set of circle projections; and 3) once the circle projection is completed, control the gantry 206 to move down and rotate (Alternatively, in the embodiment of FIG. 2F, the patient table 202 can be moved up while the x-ray source 210 and the detector 208 together are rotating), taking projections only at rotation angles 0° and 180° to acquire two line projections per rotation. It is anticipated that multiple line projections are needed to reconstruct a rather large size breast. FIG. 4 shows circular orbits C1 and C2 and positions L1, L2, L3, L4, L5, L6, L7 and L8 at which line projections are taken during one possible scan. Thus, a quasi-spiral implementation of a circle-plus-lines geometry can be provided. The key advantage of quasi-spiral implementation of a circle-plus-lines geometry is to reduce the transition time between line projection acquisition and circle projection acquisition.

Also, in a 180 degrees plus cone beam angle scan, the gantry rotates on orbit C1 or C2 over a total angle of 180 degree plus the size of cone beam angle, which is shown in FIG. 2B as θ. In a 360-degree scan or an N×360 degrees scan, the gantry moves around orbit C1 or C2 the appropriate number of times.

Figure 7A:
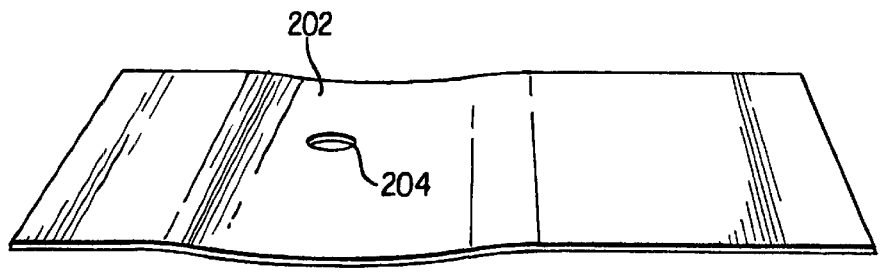
FIGS. 7A–7G show steps in the operation of the device of FIGS. 2A–2F.
Figure 7B:
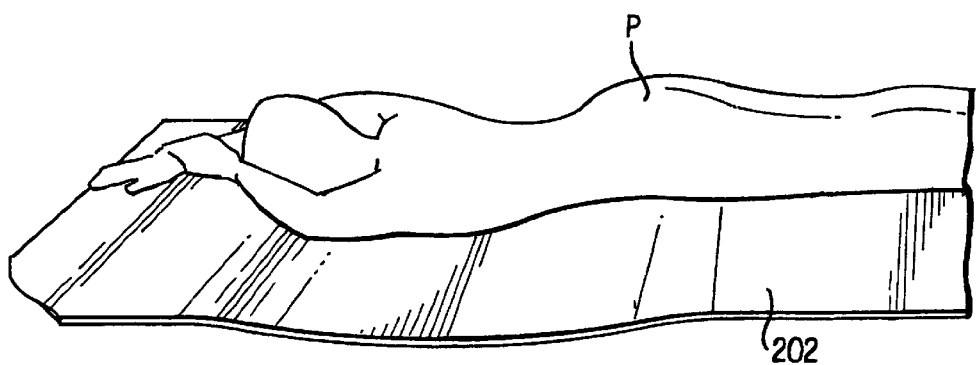
Figure 7C:
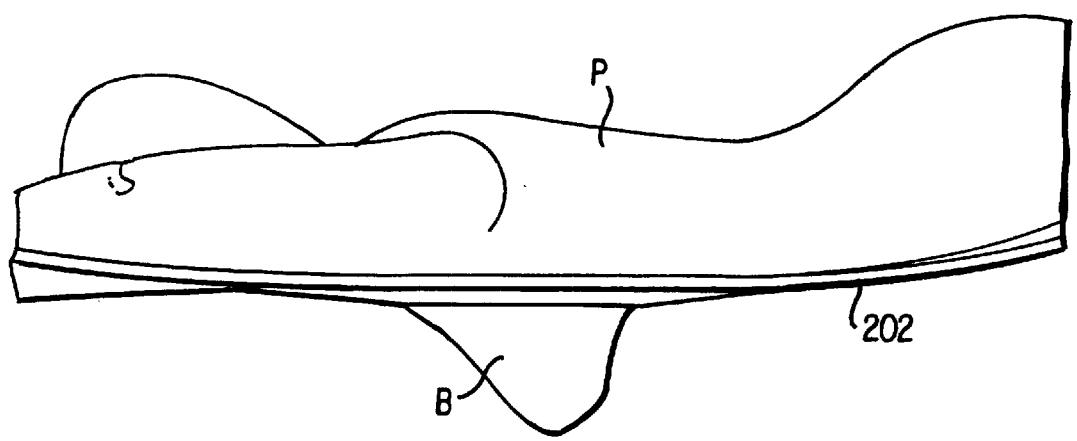
Figure 7D:
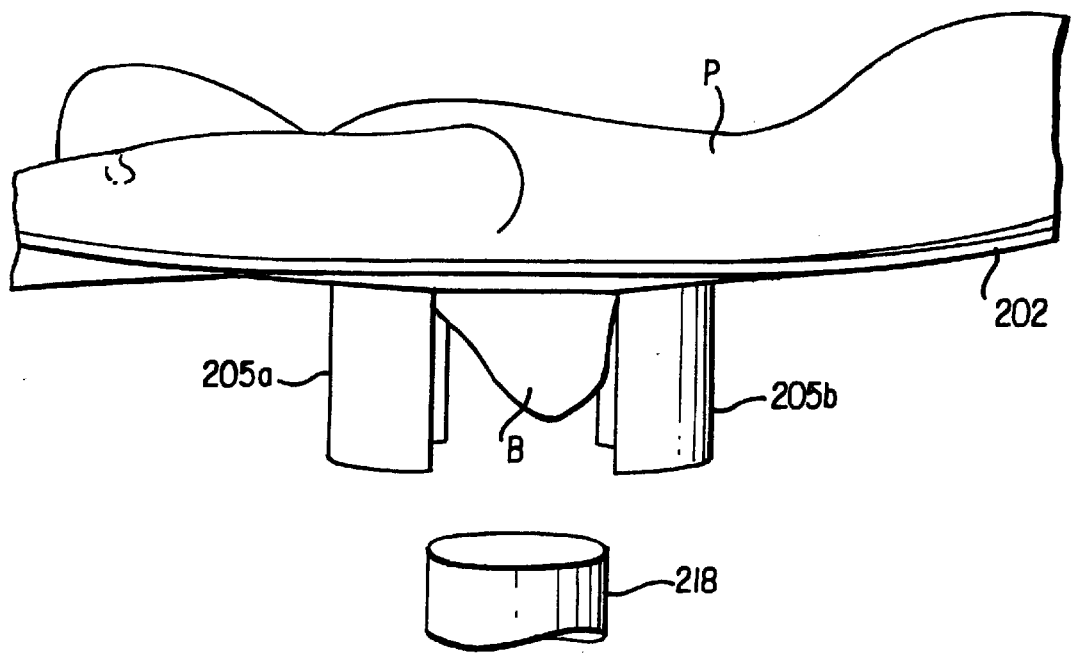
Figure 7E:
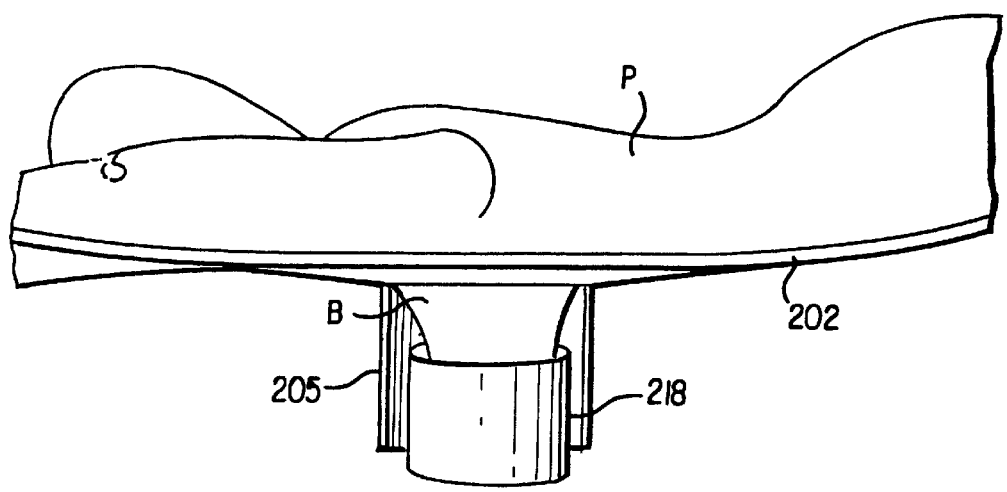
Figure 7F:
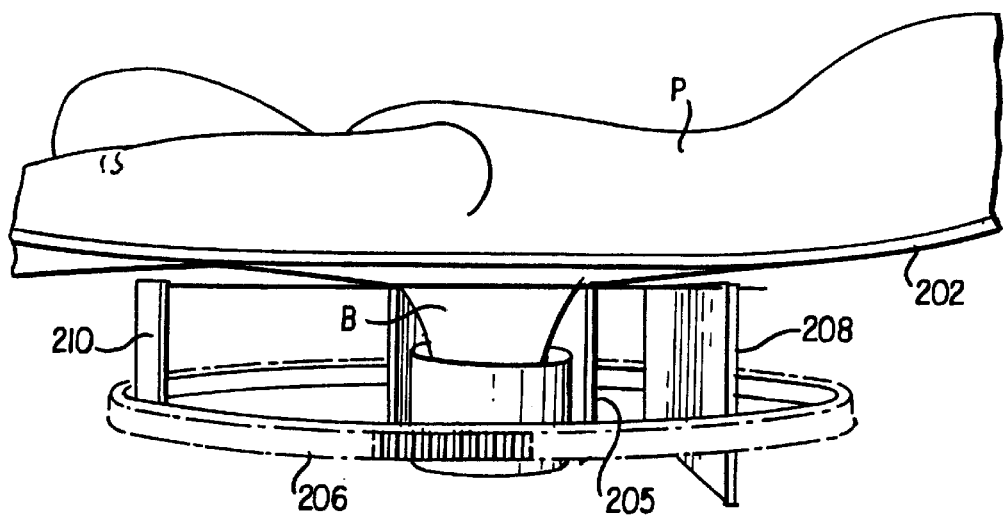
Figure 7G:
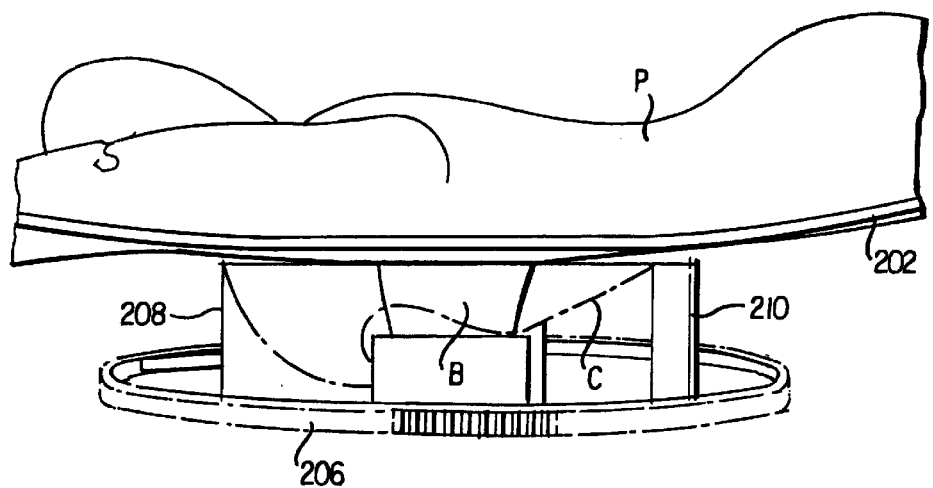

FIGS. 7A–7G show examples of the above steps. FIG. 7A shows the ergonomic table 202 with the breast hole 204. In FIGS. 7B and 7C, the patient P is lying on the table 202 with one breast B extending through the hole 204. In FIG. 7D, the breast holder 205, which is provided in two halves 205a and 205b, is placed around the breast B, and the piston 218 is placed under the breast B. In FIG. 7E, the two halves 205a and 205b of the breast holder 205 and the piston 218 are brought together to compress the breast B into the desired cylindrical shape. In FIG. 7F, the gantry 206, carrying the detector 208 and the x-ray tube 210, is placed in position around the breast B. In FIG. 7G, the gantry 206 is rotating, and the breast B is imaged by a cone beam C emitted by the x-ray tube 210. Any of the embodiments of FIGS. 2A–2F can be used in that manner.

There exist filtered backprojection cone beam reconstruction algorithms based on a circular cone beam orbit and a CPL orbit. Examples have been cited above. Such algorithms are not only computationally efficient but also able to handle a longitudinal truncation projection problem.

Unlike conventional mammography, which required hard breast compression to achieve proper image quality (with which many patients complain about pain), CBVCTM does not require hard breast compression but prefers a cylindrical formation to improve the geometric reproducibility of 3D-breast imaging. Without hard compression, the maximum thickness of the breast for CBVCTM is much larger, compared to that of conventional mammography. To achieve maximal object contrast in conventional mammography, it is desired to use very low kVp to achieve effective energies ranging from 17–23 keV, as seen from the attenuation curves of FIG. 1. While this works optimally for a compressed average size breast, using such a low kVp does not work optimally for a compressed large dense breast. This suggests that using such low effective energies (17–23 keV) will not provide enough penetration for an uncompressed breast in a CBVCTM scan. In addition, from Table 1 below, it can be seen that CBVCTM has a much wider working energy zone.

intensifier-CCD (II-CCD) detectors and flat panel detectors (FPD). A comparison of the three current large area detectors is shown in Table 2 below. As shown in Table 2, the FS-CCD detectors have only 5% to 10% DQE. That results in image noise that is significantly greater on an equivalent radiation dose basis than that achieved by a modern helical CT scanner. Image intensifiers can achieve a 50% or higher DQE within the diagnostic radiation range and can offer much better low-contrast resolution on an equivalent radiation dose basis than FS-CCD based volume imaging systems.

TABLE 2

Comparison of Three Different Area Detectors

| DETECTOR TYPE | DQE | DISTORTION | DYNAMIC RANGE | SPATIAL RESOLUTION (MM) | POSSIBLE FRAME RATE (UNITS) | VEILING GLARE |
|---|---|---|---|---|---|---|
| FS-CCD | 5–10% | No | 2000–4000:1 | 0.5 | 60 (512 × 512 × 12 bits) | No |
| II-CCD | 50–80% | 'S' & pincushion | 2000–4000:1 | 0.25–0.5 | 60 (512 × 512 × 12 bits) | Yes |
| TFT-FPD | 50–80% | No | >30,000:1 | 0.05–0.25 | 60 (512 × 512 × 16 bits) | No |

Therefore, there is much more room to make trade-offs among contrast, dose and x-ray system power output (see Table 1). We require a few hundred very short exposures in one scan. During CBVCTM imaging, the optimal kVp range and anode-filter combination are selected in order to achieve the best dose efficiency. Computer simulation indicates that the optimal effective energy range is 33–40 keV for an average uncompressed breast.

TABLE 1

Calculated Object Contrast of Breast Carcinoma in Projection Imaging and CBVCTM Imaging

| | Projection Image Contrast (%) | | | CT Image |
|---|---|---|---|---|
| keV | 3 mm | 5 mm | 10 mm | Contrast (HU) |
| 20 | 6.39 | 10.65 | 21.30 | 263 |
| 22 | 4.95 | 8.25 | 16.51 | 262 |
| 24 | 3.90 | 6.50 | 13.01 | 254 |
| 26 | 3.15 | 5.25 | 10.51 | 238 |
| 28 | 2.62 | 4.37 | 8.74 | 218 |
| 30 | 2.23 | 3.72 | 7.45 | 198 |
| 32 | 1.93 | 3.22 | 6.44 | 182 |
| 34 | 1.69 | 2.82 | 5.64 | 171 |
| 36 | 1.51 | 2.51 | 5.02 | 163 |
| 38 | 1.36 | 2.27 | 4.53 | 158 |
| 40 | 1.25 | 2.08 | 4.15 | 154 |

Initially, the volume scanning speed will be limited by the maximum frame rate of a real time FPD. The current available real time FPD has a frame rate of 60–120 frames/sec. However, flat panel researchers predict that the future frame rate can be up to 120 frames/sec. (1K×1K pixels/frame) and 480 frames/sec with reduced vertical readout lines (256×1K pixels/frame). When the frame rate of the detector is increased to 480 frames/sec. in the future, the volume scanning time of the breast will be shortened to 1–2 seconds depending on the required resolution, and/or the projection number can be increased to improve image quality. The FPD-based CBVCTM scanner represents a significant technological advancement due to using a flat panel detevtor, slip ring technology, and cone beam reconstruction algorithms that result in accurate reconstruction.

There are three types of electronic imaging area detectors: fluorescent screen-CCD area detectors (FS-CCD), image However, an II-CCD-based system has some disadvantages such as bulky size, which is not suitable for mammography, limited dynamic range (1000–3000:1), geometric distortion (pincushion and S distortions) and veiling glare, which limit further improvement in low-contrast and spatial resolution. Therefore, an FPD is preferred. The FPD can be a thin-film transistor array FPD which can acquire both static digital images (radiographic images) and dynamic images (real-time acquisition). Another preferred detector is any area detector with a resolution better than 1 lp/mm and an acquisition rate better than 5 frames per second which can acquire both static digital images and dynamic images.

Developing and optimizing an x-ray scatter control and reduction technique is one big challenge for CBVCTM because CBVCTM is less immune to scatter than fan-beam CT. CBVCTM image contrast is reduced by scatter without an effective control technique. Scatter can be countered with a hybrid technique that uses an air gap technique to control scatter an d a practical software correction technique for detected scatter. One of the major differences between fan beam slice CT and CBVCTM is x-ray beam collimation. Using very narrow slit collimation in fan beam CT reduces scatter-to-primary ratio (SPR) to 0.2 or less. On the other hand, using a large cone collimation in cone beam geometry for mammography with only an air gap technique results in an average SPR up to 1 for average breast thickness. To minimize patient dose, an antiscatter grid is not used for an average size breast. A software correction technique is used to correct for detected scatter and to reduce overall average SPR to 0.2 or less. Convolution filtering techniques and scatter detected by the FPD are used to estimate scatter distribution and then subtract it from the total projection. A known convolution filtering technique taught in Love, L. A., and Kruger, R. A., "Scatter estimation for a digital radiographic system using convolution filter," Med. Phys. 1987; 14(2):178–185, was implemented for an image intensifier-based imaging system and produced an average percentage error of 6.6% for different anatomy and different clinical applications. That is equivalent to a reduction of SPR by a factor of up to 14. Even better scatter correction results can be achieved for an FPD-based system because there is no veiling glare component, compared to an II-based system where that is a more dominant component. Based on previous studies and preliminary results, it is anticipated that the average SPR in each cone beam projection can be reduced to 0.2. That is the equivalent SPR achievable in a fan beam slice CT, using a hybrid scatter correction technique (software correction plus air gap). That analysis and the preliminary results show that with the above-noted x-ray scatter reduction and correction techniques, the FPD-based CBVCTM system provides more than adequate low contrast resolution for breast cancer detection.

The preferred embodiment combines an air gap technique with an antiscatter grid and a software correction technique for residual scatter. A 10–15 cm air gap technique is an effective method to prevent large angle scatter radiation from reaching the detector and to reduce average SPR to less than 1. It is contemplated that in the CBVCT system, the distance from the rotation center to the detector will be 20 cm. With that geometry, the air gap is more than 15 cm to achieve an average SPR less than 1.

The residual scatter present within the projection images is removed based on a convolution-filtering method to estimate residual scatter distribution in each projection image. In the convolution filtering method, residual scatter is modeled as a low pass, spatially filtered version of the total projection (scatter plus primary). After estimating residual scatter in each projection, the residual scatter radiation is then subtracted to obtain primary distribution for reconstruction. That technique effectively reduces SPR from 1.0 to 0.2 or less.

Figure 5A:
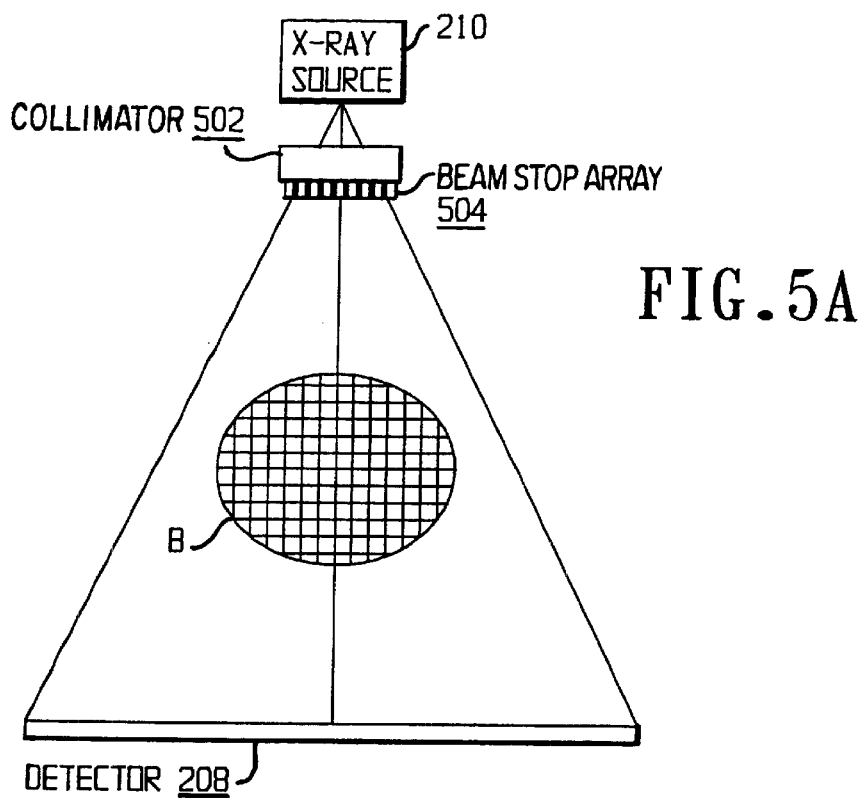
FIGS. 5A and 5B show a setup for taking scout images for scatter correction.
Figure 5B:
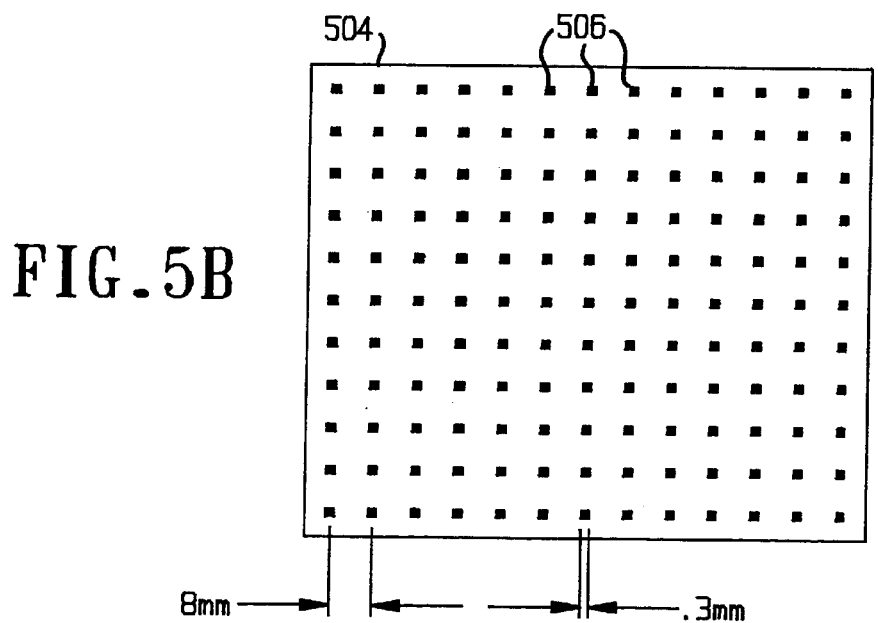

The conventional convolution filtering method requires two x-ray projections at each projection angle to accurately estimate residual scatter: one with a beam stop array for calculating two scaling factors and another without the beam stop array. That is not practical and would significantly increase patient dose in CBVCTM. To overcome those difficulties, the preferred embodiment uses scout images for estimating scatter distribution in "real time" for each patient. Before starting to scan, one scout projection image is acquired, as in a standard fan beam CT. Traditionally, the scout images are used for positioning, and surveying body size to adjust the x-ray exposure levels in real time and reduce patient dose (as with 'Smart Scan™' in a GE helical CT). Before acquiring scout images, as shown in FIGS. 5A and 5B, a square matrix 504 of small lead ball bearings 506 is placed between the x-ray collimator 502 and the breast B. Both primary and sampled scatter distributions are estimated from the scout images with the lead beam stop array. The estimated primary images are used for a scouting purpose. The scaling factors for estimating scatter distribution and the convolution kernels at sampled angle positions can be determined. Then the scatter distributions are estimated using the convolution kernel at corresponding angle positions and subtracted from the detected projections. To reduce radiation dose to the patient and computation load, only a minimum number of required scout images are acquired. Only one or two scout images are needed because after being compressed, the breast has a cylindrical shape and when convolution filtering is applied to different anatomy, the accuracy of the method is not highly dependent on the exact shape of the convolution kernel, so long as its dimensions are large enough.

The exponential kernel is used for the estimation of residual scatter because a 2D exponential kernel is an optimum formation. The same 2D exponential kernel is used for all the projections since after being compressed, the breast has a cylindrical shape and the scatter distribution is almost unchanged with angle positions.

Another technique which can be used in the present invention to improve detection of breast tumors is the ultra-high-resolution volume-of-interest (VOI) reconstruction mode, which is analogous to magnified mammography. That technique can be used to focus on a suspicious lesion.

It is known in the art for flat panel detectors to have zoom modes. One source of such flat panel detector is Varian Imaging Products of Mountain View, Calif., U.S.A.

The zoom mode of a flat panel detector such as a Varian flat panel detector is used to acquire projection data for ultra-high VOI reconstruction. In the zoom mode, the detector can acquire a random block of 768×960 pixels at 30 frames/sec. with the full 4 lp/mm resolution of the sensor. The pixel size of the detector is 127 $\mu$m. A dual-focus spot x-ray tube is used, having focus spots of 0.1 and 0.3 mm. Ultra-high-resolution VOI can use a 0.3 mm focus spot, so that the focus spot size will not be a limiting factor of the spatial resolution for the VOI mode. Therefore, the FOV (field of view) of the zoom mode is 9.75×12.2 cm. To reduce unnecessary radiation to the patient, a collimator limits the radiation to within the ROI (region of interest) in the VOI acquisition. A narrow strip of collimation (~2 cm wide) is needed. If the breast is larger than 12.2 cm in diameter, the projection data acquired in ultra-high VOI mode are truncated in the lateral direction. There are some streak artifacts if the reconstruction is obtained from the truncated data without preprocessing the data. The conventional method to deal with truncated projection data is to tail the projection data with a cosine wave before filtering. Fortunately, in the present case, the complete information in the region out of VOI is already available from the previous lower resolution scan. That information can be used to tail the truncated projection data and then complete the VOI reconstruction. Computer simulation indicates that such an algorithm eliminates the reconstruction artifacts introduced by truncated data within VOI. Such a technique is anticipated to be better than the conventional method. It is further anticipated that the ultra-high-resolution VOI reconstruction technique can provide up to 5.0 lp/mm resolution with a justifiable increase of the x-ray dose. The above-disclosed VOI technique can be used to detect other cancers, such as lung cancer.

Another use for CBVCTM is in detecting volume growth. One known indicator of malignancy is rapid growth of the tumor. Since benign tumors are characterized by lack of growth, monitoring the rate of change of the volume growth of a tumor can identify whether it is malignant and in need of immediate removal. The accurate assessment of volume growth rate of tumors can be used to predict the doubling time of the tumor and is very helpful for physicians to make diagnostic and treatment decisions.

A volume of interest is scanned, and a 3D reconstruction matrix is obtained. Then an automatic detection algorithm is used to detect tumors, and a 3D segmentation is performed on all the detected tumors. Once the 3D segmentation is completed, the volume for each tumor is determined by counting all the voxels that are determined to belong to the tumor in the segmentation procedure. A known software package to perform such functions is the "ANALYZE" 3D display software package with 3D segmentation software. Volume growth can be determined by performing the same procedure at different times and comparing the volume.

Volume growth measurement is significantly more sensitive than diameter growth because volume changes as a function of the cube of the diameter. The proportional change in the breast tumor volume is much greater than the proportional change in the tumor diameter. Thus, a CBVCTM-based volume growth measurement technique more accurately determines the change of a breast tumor, compared to conventional mammography which is only able to estimate the diameter change when the change is relatively large.

Figure 6A:
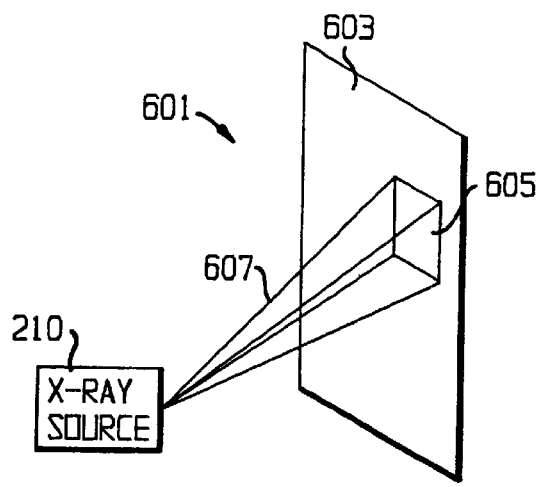
FIGS. 6A–6C show schematic diagrams of a dynamic collimator for use with the scanner of FIGS. 2A–2F.
Figure 6B:
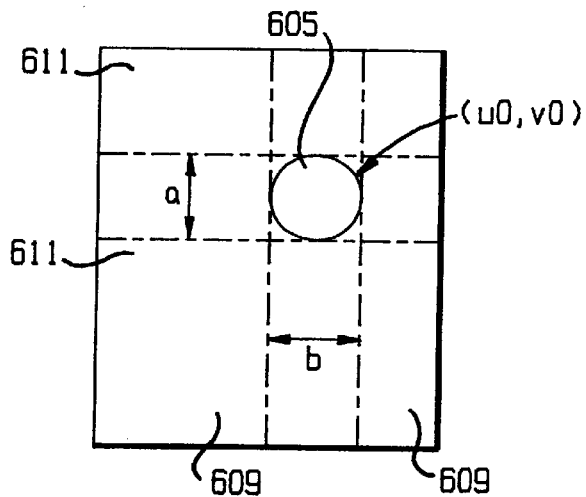
Figure 6C:
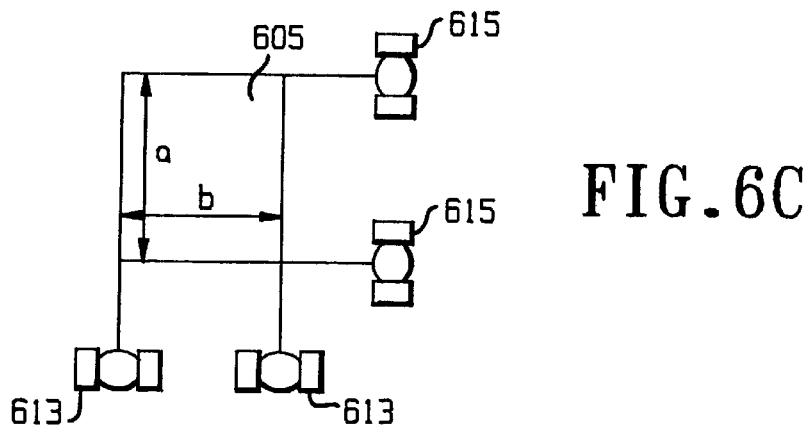

FIGS. 6A–6C show a dynamic collimator 601 usable with CBVCTM in any of the embodiments disclosed above. The dynamic collimator can be used to reduce unnecessary radiation to a patient while acquiring routine projection data for routine CBVCTM reconstruction and/or ultrahigh spatial resolution projections for VOI reconstruction. The dynamic collimator 601 includes a collimator body 603 of lead or another suitable material with an aperture 605 therein for admitting only a desired portion 607 of the x-rays emitted by the x-ray source 210. The collimator body 603 can be formed in any suitable manner, but it is preferably formed with two lead leaves 611 spaced apart by a distance a and two lead leaves 609 spaced apart by a distance b. Thus, the aperture 605 has a rectangular shape of dimensions a×b. Stepper motors 613, 615 move the collimator body 603 in two orthogonal directions to center the aperture 605 on coordinates (u0, v0) corresponding to the center of the volume of interest. With the collimator 601, x-rays radiate only the ROI for routine CBVCTM reconstruction and/or ultrahigh resolution acquisition, and routine CBVCTM reconstruction images and/or ultrahigh resolution reconstruction images can be obtained. The stepper motors 613, 615 also control the spacing between each pair of leaves so that a and b can be varied.

Table 3 below shows a comparison of helical CT, MRI and CBVCTM, assuming that a 12 cm segment of an object is scanned. CBVCTM allows higher resolution and shorter scanning time in comparison with the other modalities.

TABLE 3

Comparison of Helical CT, MRI and CBVCTM

| Modality | Volume scanning time, seconds | Resolution in x and y, mm | Resolution in z, mm |
|---|---|---|---|
| Helical CT | 15–120 | 0.5 | 1.0 |
| MRI | 30–400 | 0.7 | 0.7 |
| CBVCTM | 2.4–9.6 | 0.1–0.25 | 0.1–0.25 |

Experimental results indicate that the smallest carcinoma detectable using CBVCTM imaging is 1 mm in diameter and the smallest calcification is 0.2 mm in diameter with the equivalent radiation dose of 240 mRad and reconstruction voxel size of 0.36 mm. The results imply that with the total dose level less than that of a single screening mammography exam (assuming two views are required for each breast) for an average size breast, CBVCTM imaging is able to detect a few millimeter carcinoma and 0.2 mm calcification. With such a radiation dose level and such detectibility, the patient benefit-to-risk ratio can be over 800:1.

Other advantages of the invention will now be explained with reference to FIGS. 8A, 8B and 9A–9C.

CBVCTM provides the ability to form three-dimensional images, while traditional mammography is limited to two dimensions. Such separation would be impossible in a two-dimensional image.

Figure 8A:
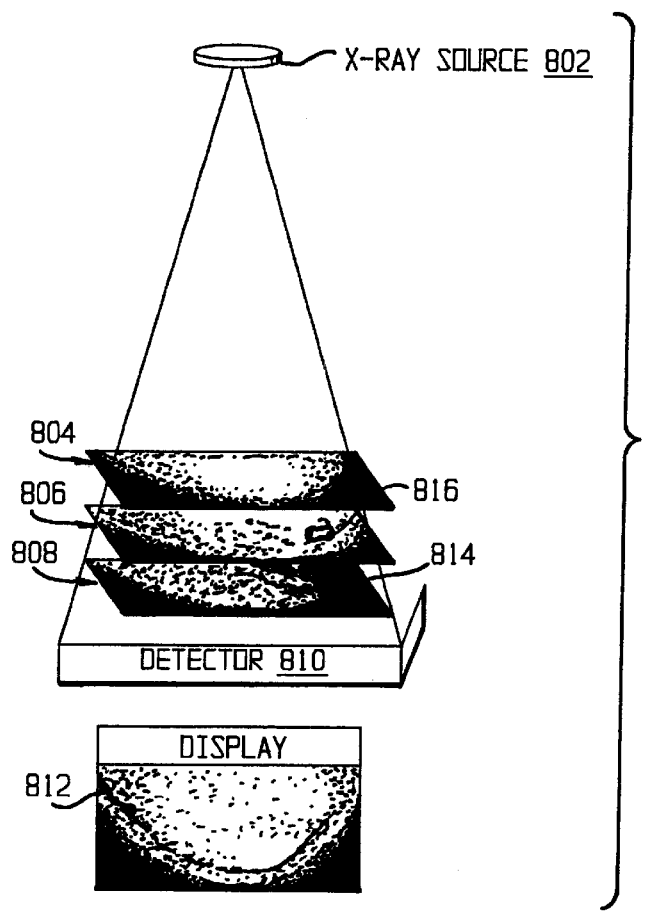
FIG. 8A shows a problem in conventional mammography techniques in which a lesion in one plane of the mammography image cannot be separated from another object in another plane of the image.

More specifically, as seen in FIG. 8A, a conventional mammography technique uses an x-ray source 802 to image planes 804, 806 and 808 of the breast on a detector 810. The resulting two-dimensional display, shown as 812, always has an overlap problem and consequently has limited sensitivity and specificity of breast carcinoma detection. More specifically, a lesion 814 in plane 808 cannot readily be distinguished from an overlapping other object 816 in plane 806.

Figure 8B:
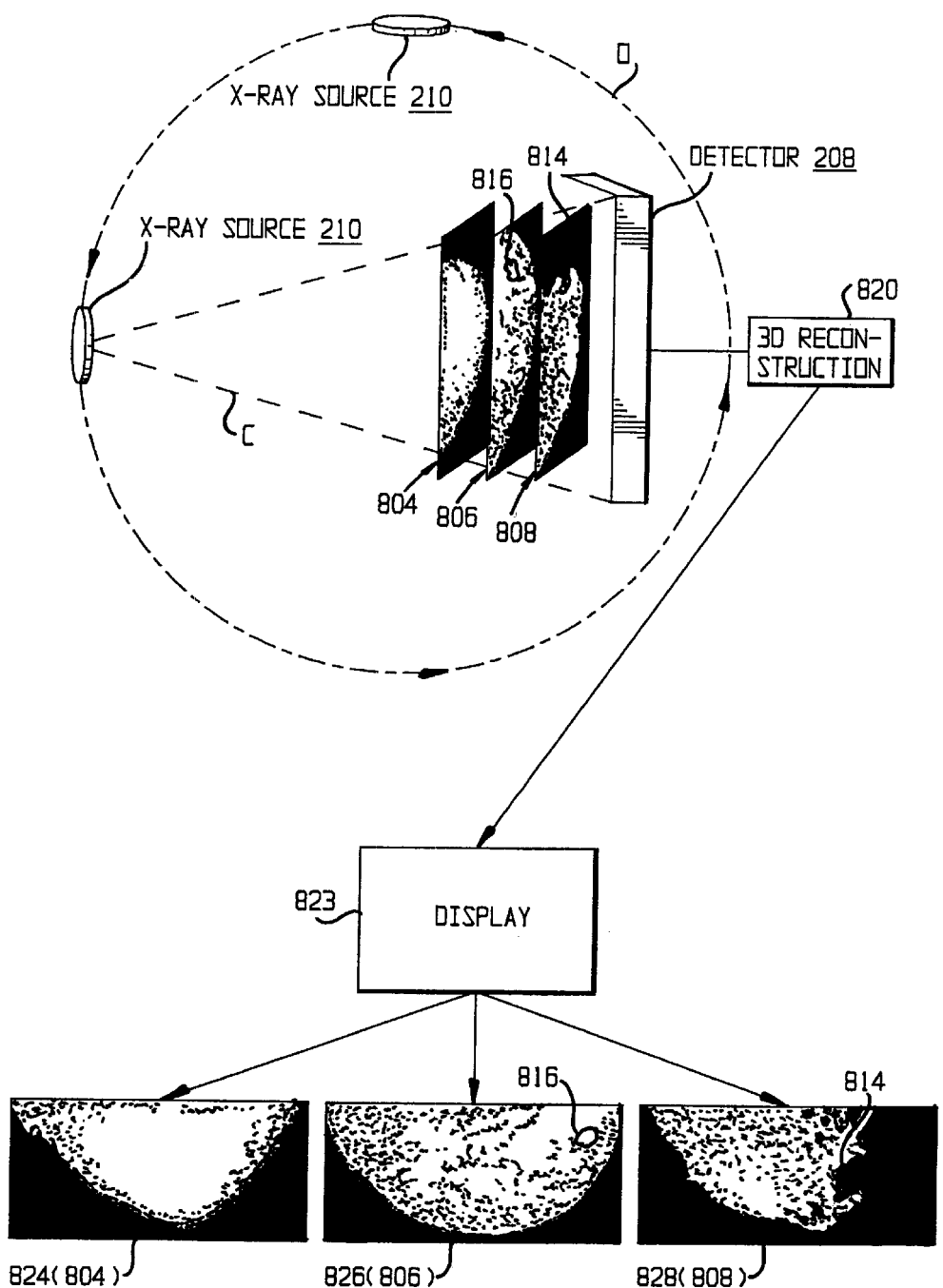
FIG. 8B shows the separation of a lesion in one plane of the CBVCTM image from another object in another plane of the image.

By contrast, as shown in FIG. 8B, CBVCTM provides a three-dimensional image including separate imaging of the planes 804, 806 and 808. After the three-dimensional reconstruction step 820 and the display step 822, the three planes 804, 806 and 808 are imaged in separate images 824, 826 and 828. Thus, the lesion 814 can be isolated from the overlapping other object 816. Accordingly, CBVCTM reconstruction images isolate superimposed planes and significantly improve the sensitivity and specificity of breast carcinoma detection compared with the conventional projection mammography of FIG. 8A.

Of course, the showing of only three planes is for illustrative purposes and should not be construed as limiting the invention.

Figure 9A:
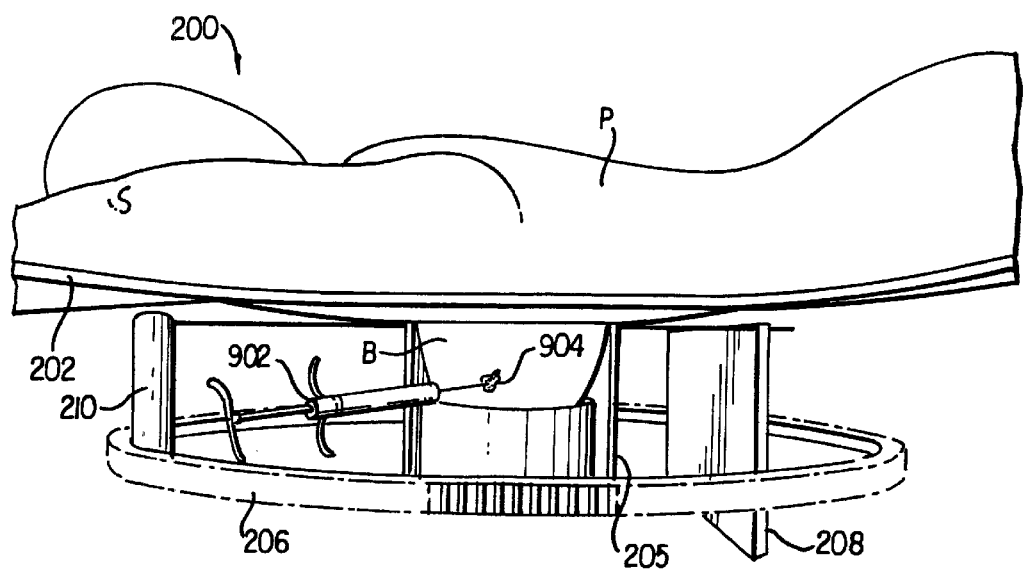
FIG. 9A shows a use of the three-dimensional CBVCTM scanner in guiding a needle during a biopsy.
Figure 9B:
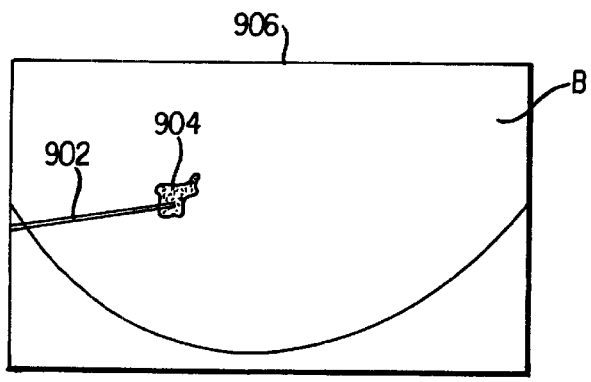
FIG. 9B shows a real-time two-dimensional image taken with the scanner of FIG. 9A.
Figure 9C:
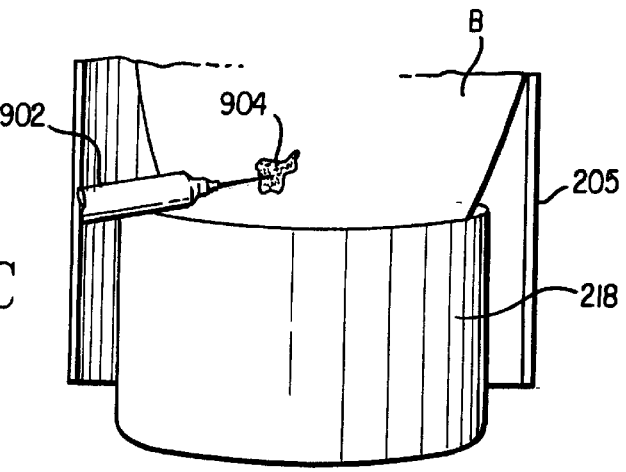
FIG. 9C shows image fusion of two-dimensional real-time images such as that of FIG. 9B with three-dimensional reconstruction.

Further, three-dimensional imaging can be used in image guided biopsy techniques. For example, as shown in FIG. 9A, the scanner 200 is used to guide a biopsy needle 902 to a lesion 904 in the patient P's breast B. FIG. 9B shows a real-time two-dimensional image taken with the scanner 200, in which the biopsy needle 902 and the lesion 904 are shown in the breast B. FIG. 9C shows image fusion of two-dimensional real-time images such as that of FIG. 9B with three-dimensional reconstruction. With the three-dimensional reconstruction of FIG. 9C, the biopsy needle 902 can be guided toward the lesion 904 in three dimensions.

While a preferred and variations thereof have been set forth above in detail, those skilled in the art who have reviewed the present disclosure will readily appreciate that other embodiments are possible within the scope of the present invention. For example, radiation other than x-rays can be used. Also, image analysis techniques such as those taught in U.S. Pat. No. 5,999,587 to Ning et al, whose disclosure is hereby incorporated by reference, can be used. Therefore, the present invention should be construed as limited only by the appended claims.

What is claimed is:

1. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector; the support comprising a table on which the patient lies while the mammography projection images are taken;

wherein the at least one motor moves the gantry frame so that the flat panel detector takes a volume scan of the breast; and wherein the table has two breast holes for both of the patient's breasts.

2. The device of claim 1, wherein the gantry is moved to image both of the patient's breasts simultaneously.

3. The device of claim 1, wherein the gantry is moved to image one of the patient's breasts at a time.

4. A method of developing a three-dimensional tomographic mammography image of a breast, the method comprising:

(a) providing a device for performing volume tomography imaging, the device comprising a cone-beam radiation source and a flat panel detector;

(b) disposing the breast in a path of cone-beam radiation between the source and the detector;

(c) using the device to obtain a volume scan of the breast, the volume scan resulting in image signals; and (d) forming the three-dimensional tomographic mammography image from the image signals;

wherein step (c) comprises moving the cone-beam radiation source and the flat panel detector to define a data acquisition geometry.

5. The method of claim 4, wherein the data acquisition geometry is a circle geometry.

6. The method of claim 4, wherein the data acquisition geometry is a spiral geometry.

7. The method of claim 4, wherein the data acquisition geometry is a circle-plus-line geometry.

8. The method of claim 7, wherein the circle-plus-line geometry comprises a single line.

9. The method of claim 7, wherein the circle-plus-line geometry comprises a plurality of lines.

10. The method of claim 4, wherein the data acquisition geometry is a 180° plus cone angle circle scan.

11. The method of claim 4, wherein the data acquisition geometry is a 360° scan.

12. The method of claim 4, wherein the data acquisition geometry is a scan over N×360°, where N is a positive integer.

13. The method of claim 7, wherein the circle-plus-line grometry is a quasi-spiral geometry.

14. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector;

wherein the at least one motor moves the gantry frame so that the flat panel detector takes a volume scan of the breast;

wherein the source comprises a controller for controlling at least one of an exposure pulse length, an exposure timing and exposure pulse numbers of the cone-beam radiation; and wherein the controller dynamically changes an exposure level of the radiation.

15. A method of developing a three-dimensional tomographic mammography image of a breast, the method comprising:

(a) providing a device for performing volume tomography imaging, the device comprising a radiation source and a flat panel detector;

(b) disposing the breast in a path of radiation between the source and the detector;

(c) using the device to obtain a volume scan of the breast, the volume scan resulting in image signals; and (d) forming the three-dimensional tomographic mammography image from the image signals;

wherein step (c) comprises taking at least one scout projection image for scatter projection, and wherein the at least one scout projection image is taken using a beam stop array.

16. A method of developing a three-dimensional tomographic mammography image of a breast, the method comprising:

(a) providing a device for performing volume tomography imaging, the device comprising a radiation source and a flat panel detector;

(b) disposing the breast in a path of radiation between the source and the detector;

(c) using the device to obtain a volume scan of the breast, the volume scan resulting in image signals; and (d) forming the three-dimensional tomographic mammography image from the image signals;

wherein the flat panel detector is a detector capable of acquiring both static digital images and dynamic images.

17. The method of claim 16, wherein the flat panel detector is a thin-film transistor array flat panel detector.

18. The method of claim 16, wherein the detector is a digital area detector having a resolution of more than 1 lp/mm, and being able to acquire both static and dynamic digital images.

19. A method of developing a three-dimensional tomographic mammography image of a breast, the method comprising:

(a) providing a device for performing volume tomography imaging, the device comprising a radiation source and a flat panel detector;

(b) disposing the breast in a path of radiation between the source and the detector;

(c) using the device to obtain a volume scan of the breast, the volume scan resulting in image signals; and (d) forming the three-dimensional tomographic mammography image from the image signals;

wherein:

step (c) comprises taking an image of a volume of interest in the breast using a zoom mode of the detector and further comprises taking an image of the breast using a non-zoom mode of the detector; and step (d) comprises using the image taken in the zoom mode to image the volume of interest and removing streak artifacts from the image taken in the zoom mode by using the image taken in the non-zoom mode.

20. A device for producing a three-dimensional cone beam volume computed tomography image of a breast of a patient, the device comprising:

a gantry frame;

at least one motor for rotating the gantry frame to form a data acquisition geometry for cone beam volume computed tomography so as to obtain a volume scan of the breast;

a source of cone beam radiation attached to the gantry frame to rotate synchronously with the gantry frame;

a two-dimensional area detector attached to the gantry frame to rotate synchronously with the gantry frame and the source, the detector being disposed in a path of the cone beam radiation to take image signals of the breast;

a support on which the patient rests while the image signals are taken, the support supporting the patient such that the breast is disposed between the source of radiation and the detector; and a computing device, receiving the image signals, for forming the three-dimensional cone beam volume computed tomography image from the image signals by performing a cone beam volume computed tomography reconstruction on the image signals to produce a three-dimensional attenuation coefficient distribution of the breast.

21. The device of claim 20, wherein the source outputs the cone beam radiation at an effective energy of 33–40 keV.

22. The device of claim 20, wherein the source outputs the cone beam radiation at a total dose level equal to or less than a total dose level of a single conventional mammography examination.

23. The device or claim 20, wherein the detector is a detector capable of acquiring both static digital images and dynamic images.

24. The device of claim 23, wherein the detector is a thin-film transistor array flat panel detector.

25. The device of claim 23, wherein the detector is a digital area detector having a resolution of equal to or more than 1 lp/mm.

26. The device of claim 20, wherein the at least one motor comprises motors for moving the gantry face to implement one of a circle-plus-line scan, a quasi-spiral scan and a spiral scan.

27. The device of claim 20, wherein the computing device is capable of forming the three-dimensional tomographic image with isotropic resolution.

28. A device for producing a three-dimensional tomographic mammography image of a breast of a patient, the device comprising:

a gantry frame;

at least one motor for moving the gantry frame to form a data acquisition geometry;

a source of cone-beam radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of cone-beam radiation and the flat panel detector;

wherein the at least one motor comprises a motor for moving the source and the flat panel detector to define a data acquisition geometry.

29. The device of claim 28, wherein the data acquisition geometry is a circle geometry.

30. The device of claim 28, wherein the data acquisition geometry is a spiral geometry.

31. The device of claim 28, wherein the data acquisition geometry is a circle-20 plus-line geometry.

32. The device of claim 31, wherein the circle-plus-line geometry comprises a single line.

33. The device of claim 31, wherein the circle-plus-line geometry comprises a plurality of lines.

34. The device of claim 28, wherein the data acquisition geometry is a 180° plus cone angle circle scan.

35. The device of claim 28, wherein the data acquisition geometry is a 360° scan.

36. The device of claim 28, wherein the data acquisition geometry is a scan over N×360°, where N is a positive integer.

37. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector;

wherein:

the detector has a zoom mode and takes an image of a volume of interest in the breast using the zoom mode;

the detector also has a non-zoom mode and takes an image of the breast using the non-zoom mode;

the device further comprises a computing device for using the image taken in the zoom mode to image the volume of interest; and the computing device removes streak artifacts from the image taken in the zoom mode by using the image taken in the non-zoom mode.

38. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation;

a support on which the patient rests while the mammography projection images are taken, the support supporting the patient such that the breast is disposed between the source of radiation and the flat panel detector; and a dynamic collimator for controllably collimating the radiation;

wherein the dynamic collimator comprises:

a first pair of leaves spaced apart in a first direction by a first distance; and a second pair of leaves spaced apart in a second direction by a second distance, the first and second pairs of leaves being disposed relative to each other to define an aperture extending the first distance in the first direction and the second distance in the second direction.

39. The device of claim 38, wherein the dynamic collimator further comprises motors for moving the aperture.

40. The device of claim 39, wherein the motors move the first and second pairs of leaves to vary the first distance and the second distance.

41. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation;

a support on which the patient rests while the mammography projection images are taken, the support supporting the patient such that the breast is disposed between the source of radiation and the flat panel detector;

an external computer for analyzing the image; and a slip ring on the gantry frame for providing communication between the flat panel detector and the external computer;

wherein the at least one motor moves the gantry frame so that the flat panel detector takes a volume scan of the breast.

42. The device of claim 41, further comprising a computer on the gantry frame, the communication between the flat panel detector and the external computer being carried out through the computer on the gantry frame.

43. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector;

wherein the at least one motor moves the gantry frame so that the flat panel detector takes a volume scan of the breast; and wherein the support comprises a support for supporting the breast while the patient is in a standing position.

44. The device of claim 43, wherein the gantry frame is oriented to scan the breast while the patient is in the standing position.

45. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector;

wherein the at least one motor moves the gantry frame so that the flat panel detector takes a volume scan of the breast;

wherein the support comprises (i) a table on which the patient lies while the mammography projection images are taken and (ii) a breast holder for holding the breast in the path of the radiation; and wherein the breast holder holds the breast in a cylindrical shape.

46. The device of claim 45, wherein the breast holder comprises a piston for pushing the breast to form the breast into the cylindrical shape.

47. The device of claim 45, wherein the breast holder comprises two halves for being brought together around the breast.

48. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation;

a support on which the patient rests while the mammography projection images are taken, the support supporting the patient such that the breast is disposed between the source of radiation and the flat panel detector; and means for taking at least one scout projection image for scatter correction;

wherein the at least one motor moves the gantry frame so that the flat panel detector takes a volume scan of the breast; and wherein the means for taking at least one scout projection image comprises a beam stop array.

49. A device for producing a three-dimensional tomographic mammography image of a breast of a patient, the device comprising:

a gantry frame;

at least one motor for moving the gantry frame to form a data acquisition geometry;

a source of radiation attached to the gantry frame to move with the gantry frame;

a flat panel detector attached to the gantry frame to move with the gantry frame, the flat panel detector being disposed in a path of the radiation; and a support on which the patient rests while the mammography projection images are taken, the support supporting the patient such that the breast is disposed between the source of radiation and the flat panel detector;

wherein the at least one motor moves the gantry frame so that the flat panel detector takes a volume scan of the breast; and wherein the flat panel detector is a detector capable of acquiring both static digital images and dynamic images.

50. The device of claim 49, wherein the flat panel detector is a thin-film transistor-array flat panel detector.

51. The device of claim 49, wherein the detector is an digital area detector having a resolution of more than 1 lp/mm and being able to acquire both static and dynamic digital images.

52. A method of developing a three-dimensional cone beam volume computed tomography image of a breast of a patient, the method comprising:

(a) providing a device for performing cone beam volume computed tomography imaging, the device comprising a cone beam radiation source and a two-dimensional area detector;

(b) disposing the breast in a path of cone beam radiation between the source and the detector;

(c) using the device to obtain a volume scan of the breast by synchronously rotating the source and the detector around an axis passing trough the breast to form a data acquisition geometry for cone beam volume computed tomography, the volume scan resulting in image signals; and (d) forming the three-dimensional tomographic image from the image signals by performing a cone beam volume computed tomography reconstruction on the image signals to produce a three-dimensional attenuation coefficient distribution of the breast.

53. The method of claim 52, wherein step (c) is performed at an effective energy of 33–40 keV.

54. The method of claim 52, wherein stop (c) is performed at a total dose level equal to or less than a total dose level of a single conventional mammography examination.

55. The method of claim 52, wherein, during step (c), the breast is not laterally compressed.

56. The method of claim 55, wherein, during step (c), the breast is compressed into a cylindrical shape.

57. The method of claim 52, wherein a carcinoma is detected in the breast in accordance with a difference in the x-ray linear attenuation coefficient between the carcinoma and a surrounding tissue in the breast.

58. The method of claim 52, wherein a tumor in the breast is distinguished as a carcinoma or a benign tumor in accordance with a border pattern of said tumor.

59. The method of claim 52, wherein the three-dimensional image comprises a plurality of planes, and wherein a breast tumor in one of said planes is tomographically isolated from other objects in adjacent ones of said planes.

60. The method of claim 52, wherein steps (c) and (d) are performed multiple times to measure a change in a volume of a lesion, whereby a carcinoma is distinguished from a benign tumor in accordance with different growth rates between the carcinoma and the benign tumor.

61. The method of claim 52, wherein a contrast medium is used to assess lesion vascularity and enhancement rate in a lesion in the breast, whereby a carcinoma is distinguished from a benign tumor in accordance with different contrast enhancement rates between the carcinoma and the benign tumor.

62. The method of claim 52, wherein a contrast medium is used to assess breast tumor angiogenesis non-invasively.

63. The method of claim 52, wherein the three-dimensional image obtained in step (d) is fused with real-time two-dimensional images obtained with the device in an image-guided biopsy procedure.

* * * * *

US006480565C1

(12) EX PARTE REEXAMINATION CERTIFICATE (10500th)
United States Patent
Ning

(10) Number: US 6,480,565 C1
(45) Certificate Issued: Feb. 10, 2015

(54) APPARATUS AND METHOD FOR CONE BEAM VOLUME COMPUTED TOMOGRAPHY BREAST IMAGING

(75) Inventor: Ruola Ning, Penfield, NY (US)

(73) Assignee: University of Rochester, Rochester, NY (US)

Reexamination Request:
No. 90/009,915, Jun. 13, 2011

Reexamination Certificate for:
Patent No.: 6,480,565
Issued: Nov. 12, 2002
Appl. No.: 09/640,713
Filed: Aug. 18, 2000

Related U.S. Application Data

(60) Provisional application No. 60/166,223, filed on Nov. 18, 1999.

(51) Int. Cl.
*A61B 6/00* (2006.01)
*A61B 6/06* (2006.01)
*A61B 6/03* (2006.01)
*A61B 6/02* (2006.01)
*A61B 6/04* (2006.01)

(52) U.S. Cl.
CPC ............ *A61B 6/032* (2013.01); *A61B 6/504* (2013.01); *A61B 6/502* (2013.01); *A61B 6/027* (2013.01); *A61B 6/481* (2013.01); *A61B 6/0435* (2013.01)
USPC .................................. 378/37; 378/20; 378/32

(58) Field of Classification Search
None
See application file for complete search history.

(56) References Cited

To view the complete listing of prior art documents cited during the proceeding for Reexamination Control Number 90/009,915, please refer to the USPTO's public Patent Application Information Retrieval (PAIR) system under the Display References tab.

*Primary Examiner* — Albert J Gagliardi

(57) ABSTRACT

Cone beam volume CT mammography is performed with a gantry frame on which a cone-beam radiation source and a digital area detector are mounted. The patient rests on an ergonomically designed table with a hole or two holes to allow one breast or two breasts to extend therethrough such that the gantry frame surrounds that breast. The gantry frame is rotatable so that the radiation source and the detector move in a circular orbit around the breast. In addition, the gantry frame is movable to describe a geometry other than a simple circle orbit, such as a circle plus one or more lines or a spiral.

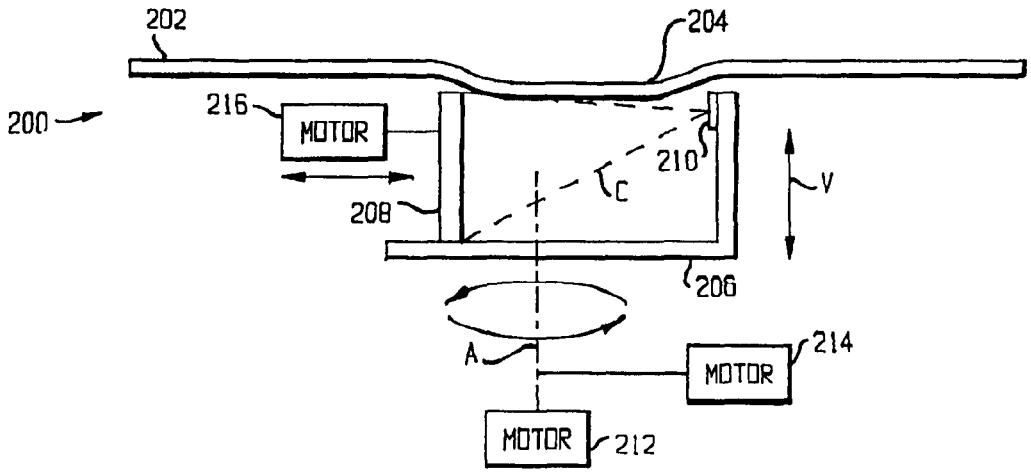

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 4-13 and 20-36 are cancelled.

Claims 1-3, 14-19 and 37-63 were not reexamined.

* * * * *